US008655679B2

(12) United States Patent
Berdia

(10) Patent No.: US 8,655,679 B2
(45) Date of Patent: Feb. 18, 2014

(54) SYSTEM AND METHODS FOR AN INTELLIGENT MEDICAL PRACTICE SYSTEM EMPLOYING A LEARNING KNOWLEDGE BASE

(76) Inventor: Sunjay Berdia, Potomac, MD (US)

( * ) Notice: Subject to any disclaimer, the term of this patent is extended or adjusted under 35 U.S.C. 154(b) by 38 days.

(21) Appl. No.: 13/205,564

(22) Filed: Aug. 8, 2011

(65) Prior Publication Data
US 2012/0035959 A1    Feb. 9, 2012

Related U.S. Application Data

(60) Provisional application No. 61/371,377, filed on Aug. 6, 2010.

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC ........................................................... 705/2
See application file for complete search history.

(56) References Cited

U.S. PATENT DOCUMENTS 5,583,758 A * 12/1996 McIlroy et al. ................... 705/2
5,737,539 A *  4/1998 Edelson et al. ................... 705/3

OTHER PUBLICATIONS

Moons, Penalized maximum likelihood estimation to directly adjust diagnostic and prognostic prediction models for overoptimism: a clinical example, 2004, Journal of Clinical Epidemiology, vol. 57, Issue 12, pp. 1262-1270.*

* cited by examiner

*Primary Examiner* — Tran Nguyen
(74) *Attorney, Agent, or Firm* — Attentive Law; Paul Ratcliffe

(57) ABSTRACT

An intelligent care provider medical practice system which learns the care provider's preferences and historical diagnosis for predicting and treating patients based on provided information. The system makes use of one or more medical knowledge bases and utilizes artificial intelligence and reasoning to learn the provider's preferences and tendencies. The system also automatically generates the provider's notes, treatment plans, and other medical practice actions for treating, billing, and processing the patient after an exam or visit.

21 Claims, 23 Drawing Sheets

Fig. 11

SYSTEM AND METHODS FOR AN INTELLIGENT MEDICAL PRACTICE SYSTEM EMPLOYING A LEARNING KNOWLEDGE BASE

CROSS REFERENCE TO RELATED APPLICATION

This application claims the benefit of U.S. Provisional Application No. 61/371,377 filed on Aug. 6, 2010 entitled "A System and Methods for an Advanced Electronic Medical Records System Employing a Learning Knowledge Base", the entirety of which is incorporated herein.

BACKGROUND OF THE INVENTION

1. Field of the Invention

The present invention relates to a system and method for an Electronic Medical Records system which utilizes a learning function associated with a care provider's preferences and tendencies in combination with a Knowledge Base.

2. Description of the Related Art

The present invention relates to electronic medical records ("EMRs") which are computerized medical records created in an organization that delivers care such as a doctor's office. The EMRs are typically part of a health information system that allows for the storage, retrieval, and manipulation of the medical records. Typically, EMRs are accessible from a workstation or in some cases through a portable or mobile device which utilizes a standard graphical user interface to retrieve, view, and update or edit the medical records.

EMRs are utilized to help manage a heavy patient load but also to assist the provider to meet the proper standards and documentation required by insurance companies before payment. The EMR systems typically require recordation of pertinent facts and findings of an individual's health and medical history including exams, tests, and treatments. A typical patient encounter includes a history taking segment, a physical exam, an analysis and diagnosis, a treatment phase, a medical record documentation phase, and a communication phase which might include instructions to the patient or a report to a referring doctor.

Currently, some EMR systems are able to monitor events and analyze patient data to predict, detect, and perhaps prevent adverse events. Such events might include pharmacy orders, lab results, and other data from services provided and from the provider's notes. However, most of these systems require significant human intervention which hinders the provider's speed of attending to patients.

Further, current EMR systems fail to provide a health information system or an electronic medical records system which automates the generation of the provider's note and learns the provider's preferences and tendencies in diagnosis and order selection as well as plans for treating patients. Current systems require the provider to either dictate notes for transcription, write down notes or type them into an EMR system all of which increase the time to process a patient diverting critical patient to doctor (or care provider) time.

Therefore, what is needed is a system which learns the doctor's preferences and tendencies in diagnosing and treating patients while automating the generation of the provider's notes, work orders, and communication.

SUMMARY OF THE INVENTION

This summary is provided to introduce concepts in a simplified form that are further described in the detailed description of the invention. This summary is not intended to identify key or essential inventive concepts of the claimed subject matter, nor is it intended for determining the scope of the claimed subject matter.

The present invention overcomes the limitations and issues of existing systems by providing an electronic medical records system which predicts a diagnosis, exam, work up, and treatment plan from a knowledge base, learns and adjusts the predicted diagnosis, exam, work up, and treatment plan based on the provider's preferences and tendencies and automatically generates the provider's medical record notes, work orders, communication and other actions for treating the patient.

Based on a patient's responses to a series of questions including, but not limited to, the body location of the problem, list of complaints/symptoms, nature of the problem, patient demographics, and practice location, the system automatically determines potential diagnoses based on probabilities utilizing a comprehensive, adaptive, and growing Knowledge Base and an artificial intelligence inference engine. Upon the provider's selection of a diagnosis, the system automatically generates a provider-specific default note, including but not limited to the chief complaint, history of present illness, past medical history, past surgical history, social history, medication, allergies, physical exam, impression, work orders, and plan. This default note is then updated by the provider as needed to put in any additional information that is specific to the current patient is that being treated. The idea of this invention is to keep this update to a minimum by learning the provider preferences and by utilization of patient inputted data through the patient portal. Upon finishing the note, the system automatically processes health insurance forms including automatically suggesting appropriate ICD diagnosis codes and CPT codes, automatically generate internal and external work orders, automatically prints out diagnosis specific patient information, generates electronic medicine prescriptions, and automatically sends out the provider note to referral providers either via email or electronic/phone FAX.

Utilizing an established Knowledge Base, that is created by a set of physician experts, and various methods of weighing and factoring the responses captured during a patient visit, the EMR and practice management system of the present invention will be able to generate a comprehensive and customizable Provider's Note which can be used by multiple departments within a medical practice and shared with other providers involved with the patient.

The implementation of the system of the present invention will reduce the total amount of time spent in capturing and generating the Provider's Note and will reduce required time to a quick review, update, and approval of the Note by the doctor or care provider. Upon doctor approval of the Note the system will then initiate the required functions of the work order generation process. Such functions might include ordering lab tests, generating prescription forms, preparing at home care notes, generating exercise and dietary information, follow on appointments, insurance forms, billing orders, and any other logical care or action which might stem from a patient visit. The system may generate the forms or generate the data which may be transmitted to a Practice Management System ("PMS") for use in billing and insurance processing systems.

The system of the present invention will: (1) capture patient information in advance of an exam: (2) retrieve Patient Medical History and provide it to the provider for review; (3) retrieve and display a set of dynamic questions based on captured patient information; (4) capture patient and provider responses to the pre-defined questions; (5) analyze the responses and data against the system's knowledge base to generate an anticipated diagnosis based on probability and artificial intelligence reasoning; (6) provide a ranked order of probable diagnoses to the care provider for selection of an actual diagnosis; (7) generate the draft doctors note based on this diagnosis and on previously learned provider-specific preferences; and (8) upon review and acceptance or modification of the doctor's note generating the required work orders based upon the final diagnosis and procedure selections.

The system of the present invention will also learn how each individual provider performs certain tasks and will adapt to those tasks or processes. All parts of the system allow learning of a provider's specific preferences. [First, the probability of a diagnosis given a certain set of patient's answers will change depending on the provider's choice of the actual diagnosis. Second, for each and every diagnosis, the system will learn and adapt to each provider's preference of the physical exam, works orders, impression, and plan. These learning activities will take place in the background after every note has been generated.

The system will also integrate with known Practice Management Systems (PMS) and/or Billing systems. The system will employ a dynamic Knowledge Base that can be general or specific such as an Orthopedic Knowledge Base. The data analysis and algorithms utilized by the system help determine the value or weight of the responses and analyze those responses against the aggregated knowledge base and the provider's learned tendencies, preferences, and processes. The system will allow the central gathering of all learned and adapted probabilities across all providers in an effort to determine global probabilities and global practice patterns.

The present invention provides an intelligent care provider medical practice system comprised of one or more servers; one or more client computers in communication with at least one of the servers; one or more databases in communication with the servers, and one or more medical knowledge bases within the databases or on the servers or computers. The system also includes one or more software applications resident on the servers or computers which provide a graphical user interface which allows entry of patient information and at least one patient health problem from the client computer; where the data is received and a comparative analysis of the patient information and patient health problem is performed against the medical knowledge base to identify one or more diagnosis. The system then calculates the probability of each of the identified diagnosis based upon a comparative analysis and then adjusts the calculated probabilities based upon a doctor or care provider's historical use profile; and then ranks the diagnoses based on the adjusted calculated probability. The ranked diagnoses can be displayed on the servers or computers and the care provider or doctor can select one of the ranked diagnoses.

The system of the present invention further records the diagnosis selected by the care provider and adjusts or updates the care provider's diagnosis profile. Upon diagnosis selection, the system or software residing on one of the servers or computers generates a Doctor's Note or care provider note. The Doctor's Note, any work orders, and treatment plans may be based upon the selected diagnosis, the doctor's preferences or profile, a suggested plan from the knowledge base, the patient information, or a combination of such information.

The system may also generate appropriate billing information and CPT codes based upon the selected diagnosis, work orders, treatment plan, and Doctor's Note.

The present invention further provides a method for predicting a diagnosis based on a care provider profile comprising the steps of: receiving patient information including at least one medical problem; analyzing the patient information and medical problem against a medical related knowledge base or database; identifying one or more diagnoses based upon the comparison; calculating the probability of each of the diagnoses; adjusting the calculated probabilities based on the care provider's historical preferences profile; and ranking the diagnoses based upon the adjusted probabilities.

The system may also display the ranked diagnosis list on a server or computer and may receive a selection of one of the diagnoses from the doctor or care provider. Upon selection of the diagnosis, the system will record the selection and update the doctor's profile and historical preferences. The system may also generate a care provider note or Doctor's Note, work orders, treatment plans, and billing information based upon the selected diagnosis. The Doctor's Note, any work orders, and treatment plans may be based upon the selected diagnosis, the doctor's preferences or profile, a suggested plan from the knowledge base, the patient information, or a combination of such information.

The system may also generate appropriate billing information and CPT codes based upon the selected diagnosis, work orders, treatment plan, and Doctor's Note.

These and other objects, features, and advantages are evident from the various aspects of embodiments of the present invention, as described in more detail below.

BRIEF DESCRIPTION OF THE DRAWINGS

The foregoing summary, as well as the following detailed description of the invention, is better understood when read in conjunction with the appended drawing. For the purpose of illustrating the invention, exemplary constructions of the invention are shown in the drawings. However, the invention is not limited to the specific methods and instrumentalities disclosed herein.

FIGS. 1-23 illustrate various systems, processes, and interface examples of the system of the present invention, wherein:

FIG. 1 illustrates a system diagram illustrating one exemplary embodiment of the present invention;

FIG. 2 illustrates a system diagram illustrating multiple medical practice groups interaction with the main computer system of the present invention;

FIG. 3 illustrates a process flow of the EMR system during the pre-appointment initial information gathering stage;

FIG. 4 illustrates a process flow for capturing patient data;

FIG. 5 illustrates a process flow of the EMR system during the knowledge base questions phase;

FIG. 6 illustrates a process flow of the EMR system during the patient exam stage;

FIG. 7 illustrates a process flow of the EMR system during the Provider Note generation stage;

FIG. 8 is a graphical user interface of a patient Login screen;

FIG. 9 is a graphical user interface of the Patient Information screen;

FIG. 10 is a graphical user interface of the Patient History screen for entry of past medical problems;

FIG. 11 is a graphical user interface of the Patient History screen for entry of family history and social history information;

FIG. 12 is a graphical user interface of the Current Visit screen for entry of the reasons for the visit;

FIG. 13 is a graphical user interface of the Current Visit screen for entry of the primary and other symptoms;

FIG. 14 is a graphical user interface of the Current Visit screen including a graphical representation of body for entry of problem location;

FIG. 15 is a graphical user interface of the Current Visit screen for entry of previous treatment;

FIG. 16 is a graphical user interface of the Current Visit screen for entry of responses to additional questions and tests;

FIG. 17 is a graphical user interface of the Appointments display including patient information;

FIG. 18 is a graphical user interface of the screen displaying the suggested diagnosis list stemming from the knowledge base analysis;

FIG. 19 is a graphical user interface of the screen suggesting various work orders for a selected diagnosis;

FIG. 20 is a graphical user interface of the display which provides an editable version of the doctor's note;

FIG. 21 is a graphical user interface of the Work Order display;

FIG. 22 is a graphical user interface of the medical practice routing slip; and

FIG. 23 is a graphical user interface of the Access Modifiers display.

DETAILED DESCRIPTION OF EXEMPLARY EMBODIMENTS

Particular embodiments of the present invention will now be described in greater detail with reference to the figures.

Figure 1:
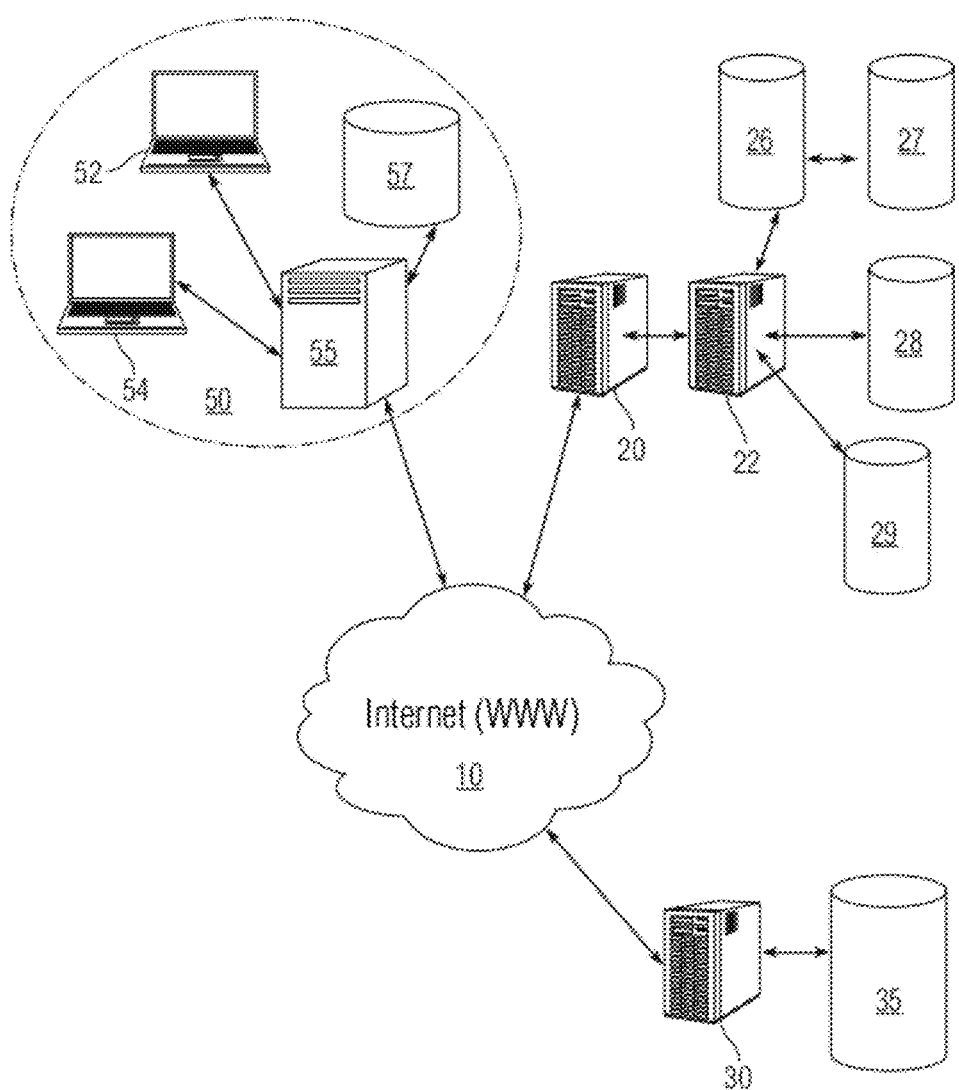
Figure 2:
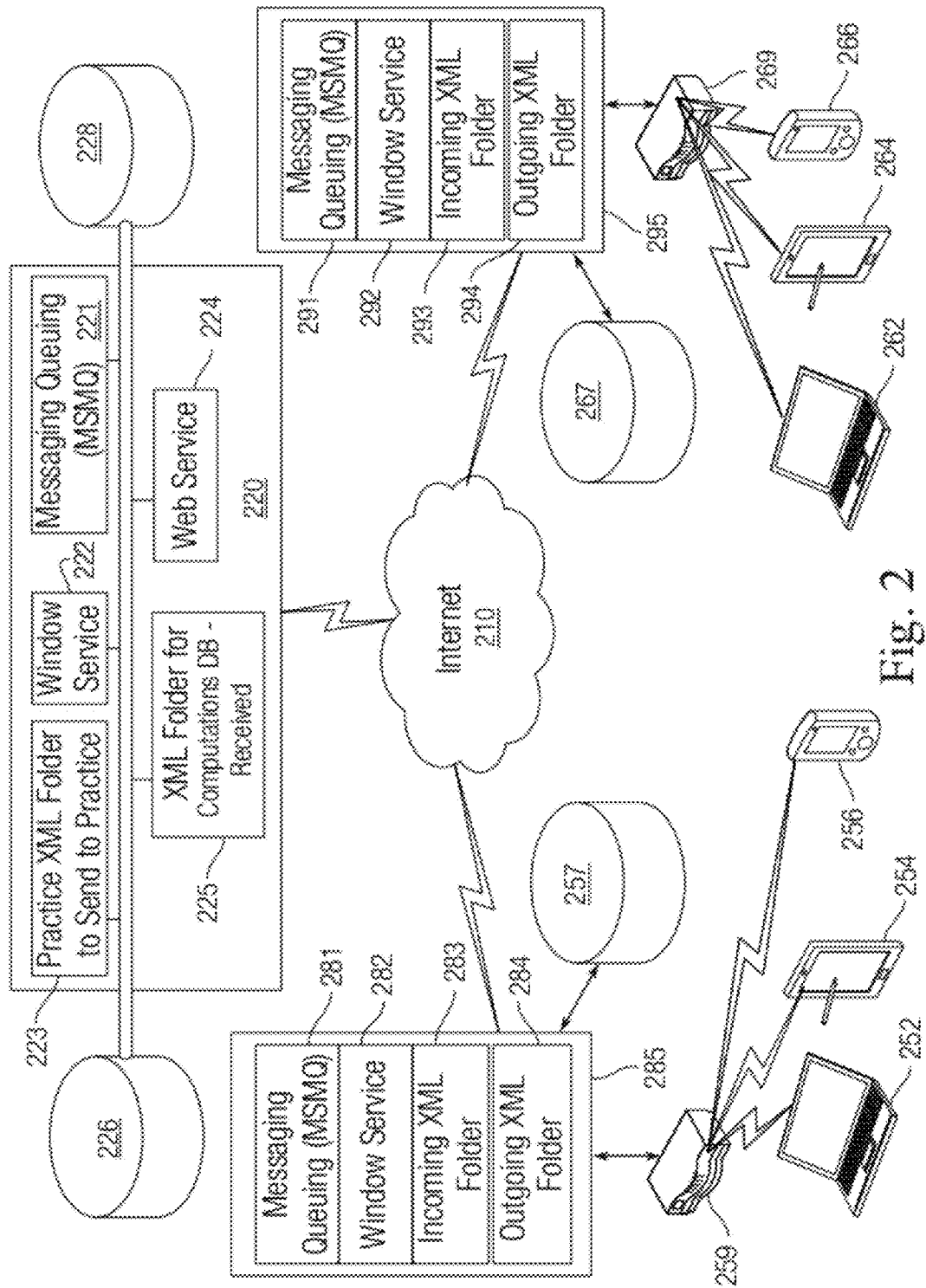

Referring now to the diagrams, FIGS. 1 and 2 illustrate an exemplary embodiment of the system of the present invention. As seen in FIG. 1, the system employs one or more servers 20, 22 which are used for providing the website or interface of the system, applications for analysis and data retrieval, as well as the structure and access to various databases. The system can include a web server 20 for running various software and applications providing the necessary graphical user interfaces, login, and logic behind interaction with the website and data. The logic would include any reasoning, algorithms, calculations and other analysis the system might perform. The web server 20 would be connected to a database server 22 such as a server running one or more SQL or MySQL installations. The database server 22 would have access to various databases 26, 27, 28, 29. The databases might include one or more knowledge base databases such as an Orthopedics Knowledge Base 26, a Pediatrics Knowledge Base database 27, or other knowledge base data sets.

The system would also include a registered user database 28 which establishes the users, types of users, and access control for each user level. The user database 28 could also include the doctor or care provider profiles and their historical interaction with the system. The historical interaction would include selection of diagnosis and selection of work orders to learn the doctor's preferences and tendencies for factoring during the diagnosis analysis phase and doctor note generation phase. The servers 20, 22 could also be connected to a database 29 with specific patient data such as the historical patient data and patient demographic data. This access might be local or remote and the system might pull or retrieve patient data as needed and add it to the EMR records within the system for each patient.

The servers 20, 22 are remotely accessed by the doctor or practice's local network 50. The local network 50 of the doctor might include a local server 55, one or more databases 57, and one or more computers, terminals, or access devices 52, 54. The local network 50 provides a means for the networked doctors, medical assistants, physician assistants, billing department, and other individuals within the practice to access local applications on server 55 and local data 57 as well as the interact with the remote servers 20, 22 of the system of the present invention. The computers or terminals 52, 54 may be desktops, laptops, notebooks, tablets, a kiosk, smart phones, or other electronic device for accessing the local network 50 in a secure manner.

Alternatively, the practice need not have a local network configuration and could have the computers or terminals 52, 54 remotely access the EMR system of the present invention as well as remotely access all patient data, billing data and other required applications. The system of the present invention might also interact with third party servers or applications 30 and data 35. Such third party systems might include access to an additional knowledge base, billing software, a CPT code database, or access to additional features and functionality. Such access might include API access to translation and transcription software, community functionality for interaction with other doctors and providers, or access to updated processors such as billing companies. Access between remote systems and components is through electronic communication such as through the internet 10. Local access between components can be through a wired or wireless connection such as through direct line or a Wi-Fi connection.

As seen in FIG. 2, the system of the present invention is designed to work with more than one medical practice units. The members of a first medical practice group would access their local system through one or more smart devices 252, 254, 256. The smart devices could be a desktop, laptop, tablet, smart phone or other communication device. The devices would mostly likely access the medical practice's system through a router 259. The router 259 could be a wireless router. The router 259 is connected to at least one computer or server 285 which includes numerous applications, folders, and files for interacting with the main system 220 of the present invention. The computer or server 285 is also connected to a database 257. The members of a second medical practice group would access their local system through one or more smart devices 262, 264, 266. The smart devices could be a desktop, laptop, tablet, smart phone or other communication device. The devices would mostly likely access the medical practice's system through a router 269. The router 269 could be a wireless router. The router 269 is connected to at least one server or computer 295 which includes numerous applications, folders, and files for interacting with the system 220. The second medical practice computer or server 295 would be connected to one or more databases 267.

In the preferred embodiment, each medical practice computer or server 285, 295 would include a windows service 282, 292 a messaging queuing service (MSMQ) 281, 291, an incoming XML folder 283, 293 and an outgoing XML folder 284, 294 for interacting with the company level system 220.

The medical practice computers or servers 285, 295 would communicate with the company level system 220. The company level system 220 could be one or more computers or servers which contain various software applications and files for interaction with the medical practice systems and for processing and analyzing data to provide updated data and analysis to medical practices and practitioners.

In a preferred embodiment, the company level system 220 would include a windows service 222, a web service 224, a message queuing (MSMQ) service 221, an XML folder for computations and data received 225, and a medical practice XML transmitting folder 223. The company level system 220 would be connected to numerous databases 226, 228. The databases 226, 228 would include one or more medical knowledgebase data sets such as an Orthopedics knowledge base or a Pediatrics knowledge base. The databases 226, 228 might also have registered user data, patient data, practitioner data and other data sets.

In one exemplary embodiment, the company databases 226, 228 would use SQL and the company level server 220 will have two folders to store xml files. A windows service 222 will run on the company server 220 to provide XML from the XML folder 225 to the web service 224. The XML folder 225 for computations stores data received from the practice groups which is then analyzed and structured for computational analysis in accordance with the present invention.

The Windows service 222 will also create and store XML files in the Practice XML folders 223 to send to the medical practice groups. The XML files to send are based on the new inserted and updated data in the company databases 226, 228. The messaging queuing (MSMQ) service 221 is configured to send the xml files in the queue. The Web service 224 is responsible for performing a create, read, update, and delete (CRUD) operation on the company databases 226, 228 based on the xml received by the windows service 222.

In use, the medical practice user will use an application resident on the smart device 252, 254, 256 to access the medical practice computer system 285, 295. In the preferred embodiment, the user belongs to a practice which will be using a common SQL Server database 257, 267 installed on practice server 285, 295. The Windows service 282, 292 will run on the Practice level server 285, 295 for sending the XML files over the internet 210 to the Web service 222 running on the Company Server 220. The Windows service 282, 292 of the practice is also responsible to perform a create, read, update and delete (CRUD) operation at the practice level after receiving the xml in the Incoming XML folder 283, 293.

The Practice level server 285, 295 will also have two folders to store XML. The Outgoing xml folder 284, 294 will store all xml files which will be created by applications after performing the CRUD operation on the practice database 257, 267. The Incoming xml folder 283, 293 will store the xml files which the medical practice group receives from the company level system 220.

The Practice level server 285, 295 will also have the message queuing service 281, 291 configured to provide message queuing for sending XML to the windows service 282, 292. Whenever any operation will be performed on a database 257, 267 at the practice level an xml file will be created and transmitted to the company level system 220. Through the network and systems of the present invention, the local medical practice groups are able to obtain patient information locally, update EMR files, and interact with the knowledge base data and analytic engine resident on the primary servers 220 and databases 226, 228.

Figure 3:
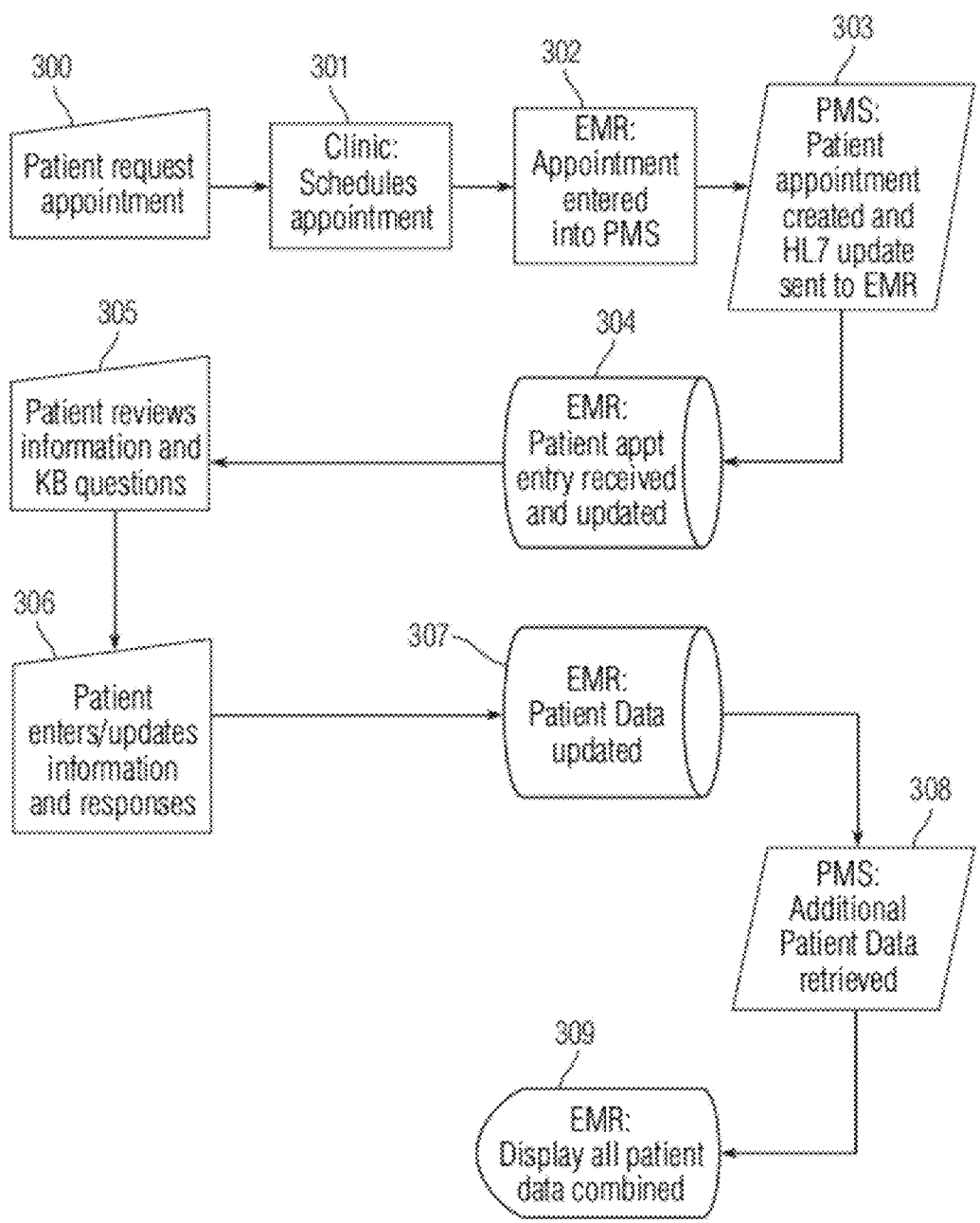

Although the system is comprised of various computers, software applications, and databases the interaction for the user is primarily through one or more user interfaces used to obtain and analyze data related to a patient's current or historical medical condition. The interfaces help establish various procedures and processes for gathering and analyzing the information. As shown in FIGS. 3-7, the various methods and procedures of the present invention are depicted. FIG. 3 provides a use flow model for receiving patient data prior to an appointment. In step 300 a patient requests an appointment. The appointment request is handled by an administrator or front desk person of a clinic or care provider practice who enters the appointment into the Practice Management System ("PMS") as shown in step 301. The appointment information is then received and added to the PMS system in step 302. The patient appointment is created and an HL7 update is sent to that patient's Electronic Medical Record ("EMR") in step 303. The patient appointment entry is received and updated in the EMR system in step 304. In step 305 the patient is provided medical history information and related data in the system for review. The patient updates any information and enters any new or relevant data in step 306. The information may be entered directly into electronic forms such as might be available at a portal or kiosk. Alternatively, the patient could provide such information remotely over the internet through a computer or the patient could provide the information on paper forms for an administrative assistant to enter. In step 307 the updated information is sent to the EMR system and the patient data is updated. The additional patient data is then retrieved and/or received by the PMS system in step 308. On the day of the appointment all data is retrieved, combined and provided to the medical practice in step 309. The retrieved data may include previously entered health information, information from other care providers, lab results and other relevant information. In an exemplary embodiment the patient is provided a kiosk or a computer terminal at the medical practice facility to provide the information and responses.

Figure 4:
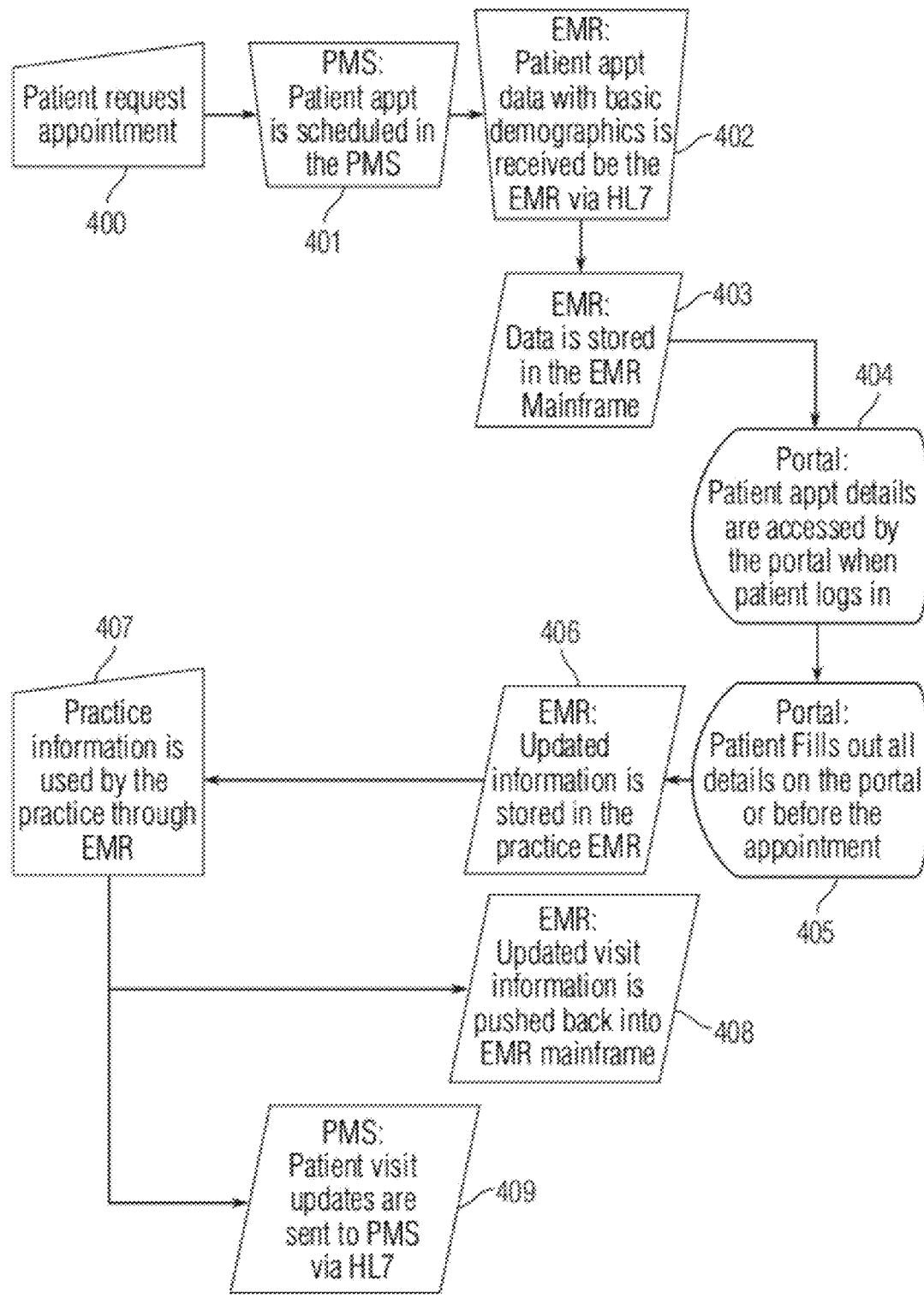

FIG. 4 shows the process and flow behind the capturing of patient data. The patient schedules their appointment in step 400. In step 401 the appointment is entered or scheduled in the PMS. In step 402, the patient's appointment data and basic demographic information is received by the EMR using Health Level Seven (HL7) standards. The system may use a different health level standard other than HL7 and still fall within the scope of the present invention. In step 403 the patient's data is stored in the EMR mainframe or database and available for use and retrieval by the system. In step 404, the patient's appointment details are accessed when the patient logs in. In step 405 the patient fills out all details about their health problem prior to the doctor's examination. Such information could be filled out using a kiosk or smart device. The information could also be entered by an assistant from manual forms or from responses to questions and interaction with the assistant. In step 406, the updated information is stored in the EMR for access by the practice.

In step 407, the medical practice members use the EMR information and PMS information to interact with the patient. Based on the patient interaction, updated visit information is generated and the care providers in the practice then provide information related to the visit. The visit information is pushed back into the EMR mainframe or database and the visit update is entered into the PMS system (step 409) and sent to the EMR system (step 408).

Figure 5:
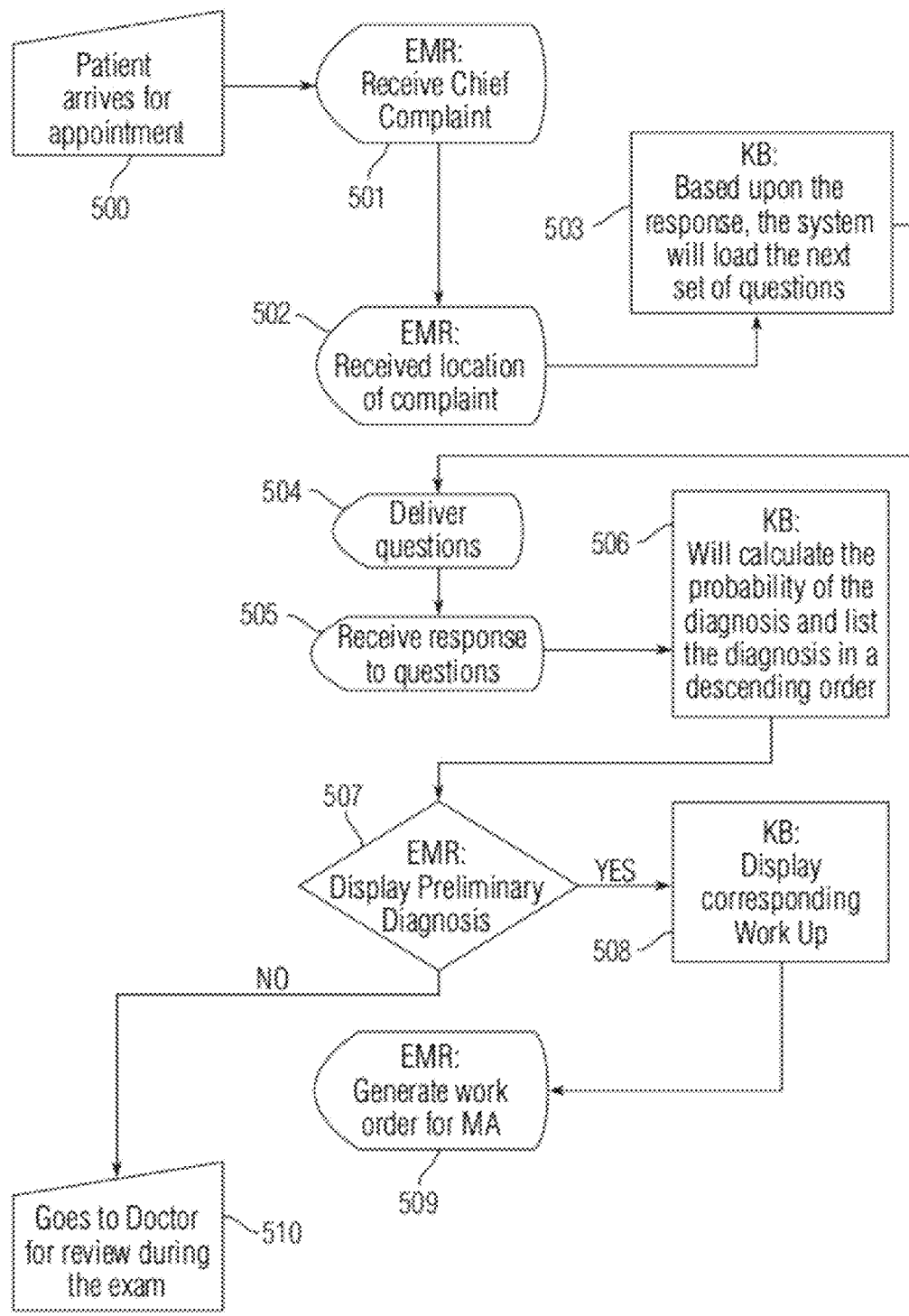

As seen in FIG. 5, the method and process of the present invention makes use of a knowledge base. The patient in step 500 provides information on their health complaint or issue including their chief complaint and the location of the complaint or medical problem. The chief complaint is entered and received by the system in step 501 and the location of the complaint is entered and received by the system in step 502. The system may allow the patient to enter specific text base responses to the location of the complaint or allow the patient to circle, or otherwise select, an area of complaint on a displayed image. Such a system enables the patient or user to select or circle a body part such as a hand, foot, arm, etc. Then the system would be able to zoom in on the image and allow the user to identify the specific area of complaint such as the heel of the foot.

Based upon the response to the chief complaint and location of the complaint, the system (step 503) determines an appropriate set of questions which are presented to the patient in step 504. The responses are received from the patient in step 505. Based upon the responses to the questions, the system in step 506 will weigh each response and compare it to the Knowledge Base ("KB") using various methodologies and an analytical engine to determine the probability of diagnosis. The system will then list the potential diagnoses in a descending order based on probability. The system may use various analytical processes and artificial intelligence methodologies to determine the probability such as Bayesian reasoning, fuzzy logic, neutral networks, or any other logical method for analyzing the patient's data against the Knowledge Base and accurately predicting probability of a diagnosis.

In step 507, the ordered list of preliminary diagnoses is then made available for display to the medical assistant or for review by the doctor during the exam. If the doctor agrees with the preliminary diagnosis the doctor indicates acceptance of the preliminary diagnosis to the system and the KB (step 508) will process and display the corresponding work up. The KB information is then used to generate the work order for the medical assistant (step 509). In the event the doctor does not agree with the preliminary diagnosis the information is then used by the doctor during the patient exam (step 510) and doctor's entered diagnosis is fed back into the knowledge base for adjusting the probabilities for that specific doctor. Thereby, the system is able to learn each doctor's preferences on identifying diagnosis and treatment plans. Further, through the aggregated information of many doctors the system can identify the most common diagnosis and treatment plans historically, seasonally, and currently and alter the probabilities accordingly.

Figure 6:
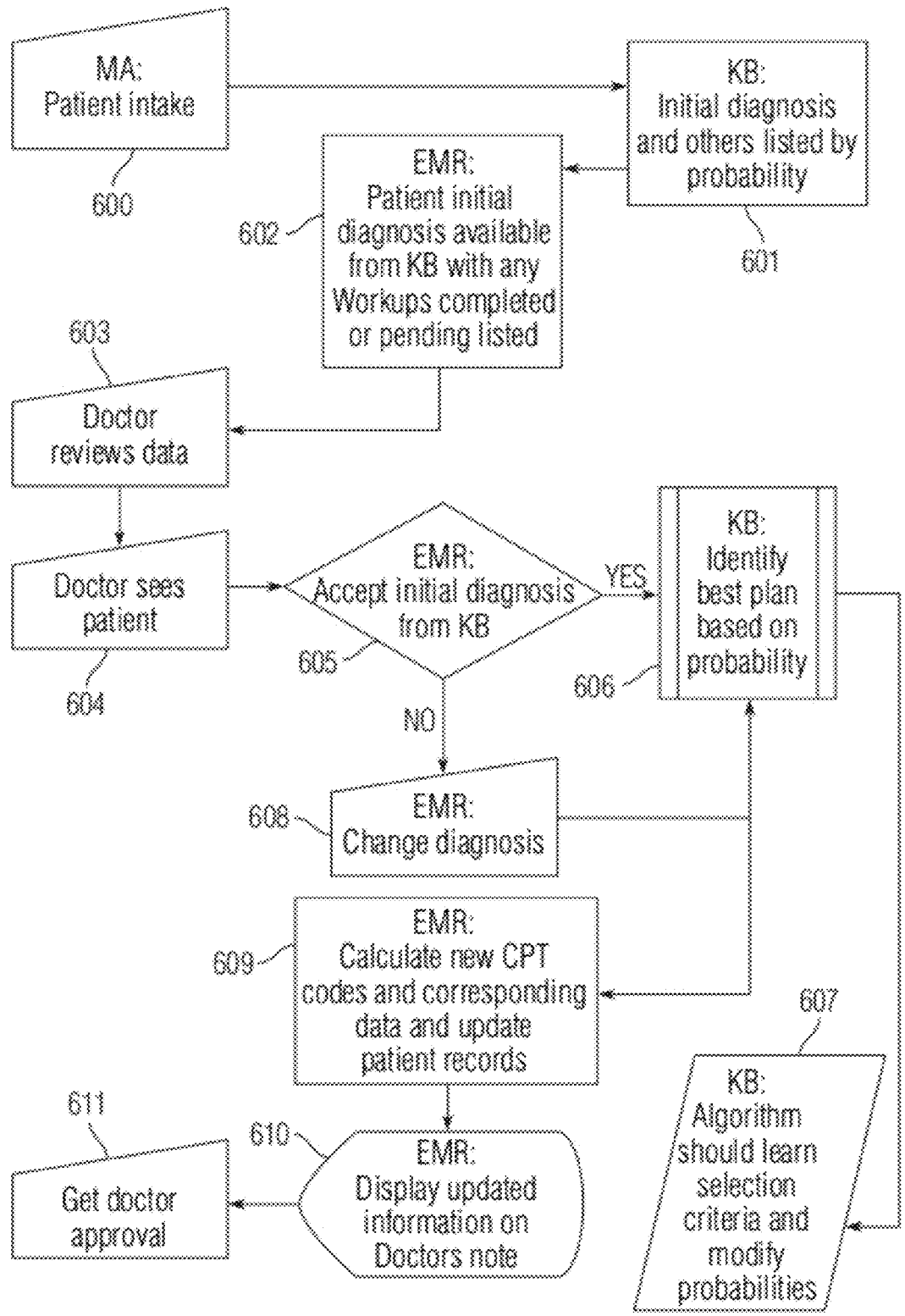

FIG. 6 details the typical flow during a patient doctor exam. During a typical exam the medical assistant processes the intake information in step 600. The KB uses the provided health and condition information to generate an Initial Diagnosis and determine other diagnoses based on probability (Step 601). The diagnoses are provided to the EMR and displayed to the medical assistant in step 602 to generate any workups or tests to be performed. In step 603, the doctor reviews the diagnosis list from the KB along with other data from the EMR. Such data might include the initial diagnosis, patient's complaint, location of complaint, patient's health history and response to questions, lab results and work orders, suggested tests and analysis, treatments and other data and information which might be useful in the treatment of the patient.

In step 604, the doctor sees and examines the patient. In step 605, the doctor is prompted by the system to either accept or reject the initial diagnosis. If the doctor accepts the diagnosis then in step 606 the system identifies the doctor's preferred plan or course of action based on probability and learned preferences of the doctor. In step 607, the doctors selected course of action is captured and the KB and associated algorithms and analytics account for and adjust the doctors preferred selection criteria and modify the probability calculations accordingly for future diagnosis and treatment analytics.

In the event the doctor does not accept the initial diagnosis from the KB in step 605 then the change diagnosis command is received by the system and the doctor is prompted to change the diagnosis (Step 608). The doctor may enter a diagnosis or search the system and KB for a diagnosis based upon keywords. The new diagnosis is entered and assessed by the KB to identify the best plan (step 606) or treatment. Further, the doctor entered diagnosis is then used by the system to calculate new ICD/CPT codes, update all corresponding data, and update the patient record in step 609. The updated information is then displayed (Step 610) on the doctor's note. The doctor is then prompted (Step 611) to approve the doctor's note. In this exemplary embodiment, the doctor interacts with the system and reviews the probable diagnosis and Doctor's Note through a wireless personal computer, tablet or mobile terminal which the doctor can utilize while assessing the patient.

When the doctor ultimately selects a diagnosis from the KB the diagnosis acceptance is added to that specific doctor's historical treatment record and utilized by the system for future determination of diagnosis rank or order. This learning function allows the system to adjust both the weighting of responses and the probability calculations for determining anticipated diagnoses.

Figure 7:
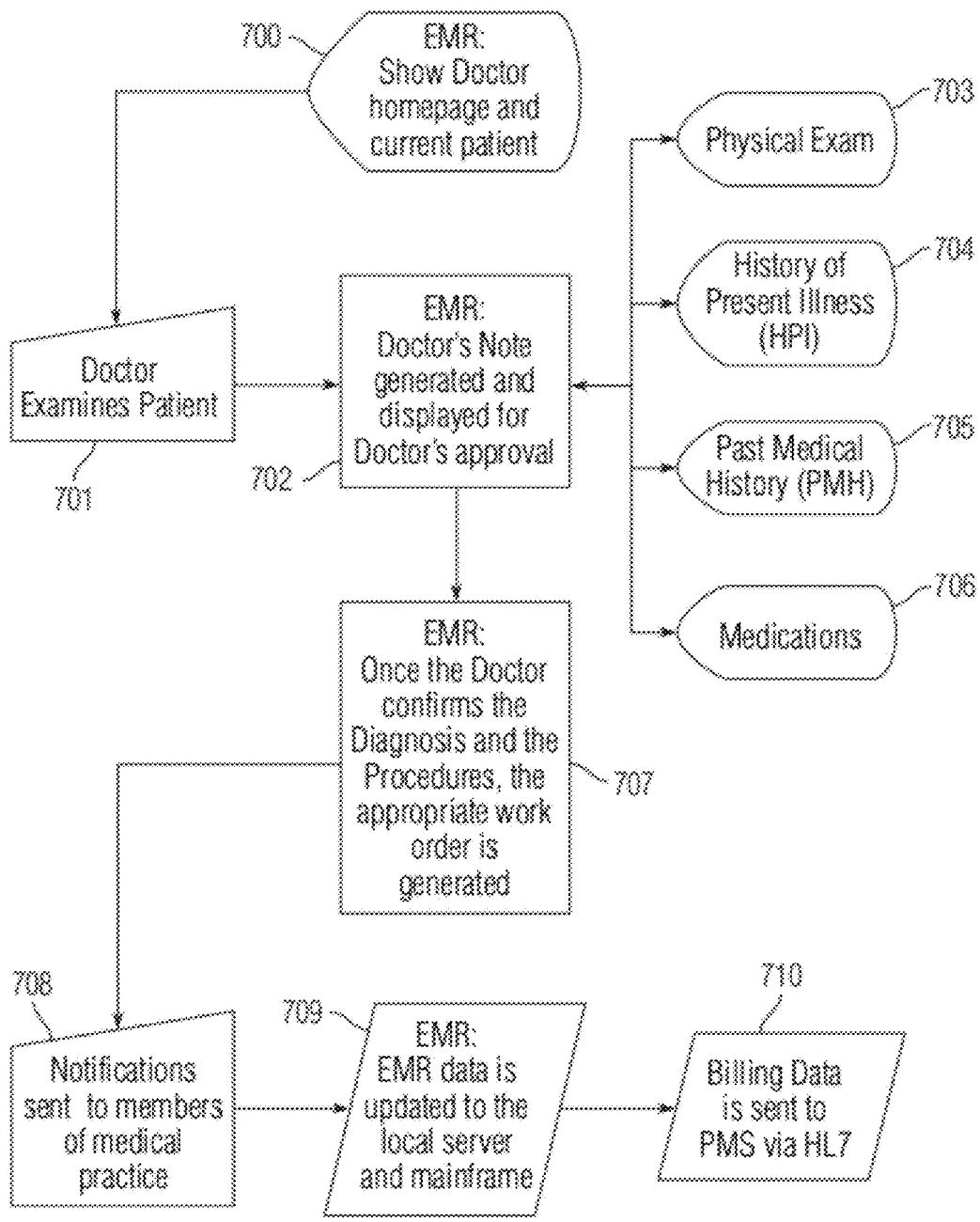

FIG. 7 depicts the process and flow for generation of the doctor's note. In step 700, the doctor is provided and reviews the EMR of the patient. The doctor then examines the patient in step 701. Upon selection of the diagnosis as previously discussed, the system in step 702 will generate a Doctor's Note which includes the chief complaint, history of present illness, past medical history, past surgical history, social history, review of systems, medication, allergies, impression, and plan. The Doctor's Note can be utilized for documentation of the patient encounter, treatment, prescriptions, requested tests, required lab work, insurance information and other information and processes which can improve the administrative flow of paperwork required by a medical office. The Doctor's Note will be viewable on the screen of the smart device or computer and might include sections for the Physical Exam 703, History of Present Illness 704, Past Medical History 705, Current Medications 706, Lab or Test Results, and other pertinent information related to the visit and the patient.

The system will also allow the doctor to review various information aspects on the diagnosis from the Knowledge Base. In addition, the Doctor's Note will be prefilled with the patient's relevant demographic information, personal data, and medical data captured through the portal or kiosk or entered by a medical assistant. The doctor will be able to navigate to various sections of the doctor's note to review, edit, or update any information.

Once the doctor finalizes and confirms the diagnosis and procedures in step 707, the system will then automatically generate provider-specific appropriate work orders. In step 708 the various work orders are saved in the system and notifications are sent to appropriate individuals in the medical practice group or external service providers for further processing if necessary. Upon generation of the work orders they will be available within the system for processing by the medical assistant, physician's assistant, the billing department and any technicians or lab assistants. In step 709, the final diagnosis and doctor's note information is added to the EMR data for that patient and is updated at both the local server and remote mainframe. Finally, in step 710, all billing and insurance orders are sent to the PMS.

By way of example, the work orders might include scheduling additional appointments or therapy sessions, ordering lab work, generation of prescription orders for signature, billing instructions upon checkout, and other relevant orders and procedures. The system of the present invention may contain pre-defined procedures and orders but can also accept orders and procedures established by the practice or any specific doctor.

An additional important aspect of the present invention is the doctor's preferred method of treatment for each diagnosis. The system includes a self learning or artificial intelligence (AI) component that learns the doctor's diagnosis selection tendencies as well as the doctor's preferred work orders and procedures for each diagnosis. Therefore, when a doctor makes a diagnosis the system can pre-select the orders it determines the doctor is likely to want and prompt the doctor for approval or inclusion of the appropriate work orders. This AI component is also complex in its application as it can apply the AI analysis on many parameters. Such parameters might include gender, age, race, height, weight, overall health, previous complaints, health history, genetic characteristics, known familial health patterns, and other relevant differences in patients. Therefore, the system is sophisticated enough to understand the doctor may have different procedures and orders for a similar complaint and diagnosis based on the patient's profile. An example of this might be the difference in work orders, procedures, and treatment of a sprained knee in a young child compared with an adult with a history of knee ailments.

To understand the analytical processing and reasoning behind the predictive diagnoses we can discuss an example using Bayesian reasoning. Suppose we have a disease and a set of n relevant symptoms or chief complaints. If we let D be a random variable that is true if the patient has the disease and is false otherwise. Similarly, $s_i$ is a random variable that is true if the patient has (or complains of) symptom i and false otherwise. The fact that having the disease causes the patient to experience the symptoms, and that the symptoms are conditionally independent given the disease (i.e., $p(s_1, \ldots, s_n|D) = \pi_i p(s_i|D)$). That is, the joint probability of having the symptoms given the disease is equal to the product of the probabilities of having each symptom individually given the disease. Or, more intuitively, if it is known that you have the flu then knowing that you have chills doesn't provide any additional information about whether you have a fever.

Suppose for the moment that the system knows the values of all symptoms (i.e., whether the patient complains of them or not). To compute the posterior probability of having the disease given this information we can solve as follows:

$$p(D|s_1, s_2, \ldots, s_n) = \frac{p(D)p(s_1, s_2, \ldots, s_n|D)}{p(s_1, s_2, \ldots, s_n)}$$

$$= \frac{p(D)\pi_i p(s_i|D)}{p(s_1, s_2, \ldots, s_n)}$$

$$= \frac{p(D)\pi_i p(s_i|D)}{\sum_d p(s_1, s_2, \ldots, s_n, D=d)}$$

$$= \frac{p(D)\pi_i p(s_i|D)}{\sum_d p(D=d)p(s_1, s_2, \ldots, s_n|D=d)}$$

$$= \frac{p(D)\pi_i p(s_i|D)}{\sum_d p(D=d)\pi_i p(s_i|D=d)}$$

First, the portion of the equation written as $p(D|s_1, s_2, \ldots, s_n)$, relates to the probability that the disease has some particular value about which I care (i.e., true) given that the symptoms have whatever values were observed or reported. However, the expression $p(s_i|D=d)$, means the probability that a symptom has whatever value was reported given that the disease variable has value d, which is imposed regardless of what is true in the world. Second, to compute exact probabilities using a Bayesian Network ("BN") structure, the system only needs to know the prior probability of the disease (p(D)). Thus, the system needs to known the probability that a randomly selected patient in the doctor's office has the disease, and the probability of having each symptom given the disease ($p(s_i|D)$ for both D=true and D=false).

Turning our attention to those instances when the system does not know the values of all of the $s_i$ variables. For example, a patient complains of pain but does not answer the question provided by the system about redness, or the question is not posed for some reason. It is important to know the difference between not having symptom i, in which case $s_i$=false, and not knowing whether the patient has the symptom, in which case we don't know the value of $s_i$.

Assuming the system does not know the value of just one $s_i$ and, without loss of generality, that i=1. The system proceeds as follows:

$$p(s_2, \ldots, s_n|D) = \sum_{v \in s_q} p(s_1, s_2, \ldots, s_n|D)$$

$$= \sum_{v \in s_q} p(s_{q1} = v|D)\pi_{i>1} p(s_i|D)$$

$$= 1 \times \pi_{i>1} p(s_i|D)$$

$$= \pi_{i>1} p(s_i|D)$$

If the system doesn't know the value of a symptom's random variable, then we can remove it from the product. This works only in the special case of the BN structure above. The system can follow the same line of reasoning with more complex BN structures, but in the general case dropping terms in the product does not produce correct results.

To make all of this concrete, let's consider a scenario in which there are only two diagnosis, paronychia (P) and felon (F), and that every person who comes to the doctor's office has one or the other, with paronychia occurring 60% of the time. The baseline knowledge base indicates that 60% of patients have P, and thus 40% do not. Using a medical related knowledge base and several assumptions we can start to determine probability. The knowledge base also provides that the probability of having a symptom is low when the disease is not present. For example, the probability of having no pain with Paronychia is only 20% or 0.2 when P=no. Accordingly, the probability of having no pain with something other than Paronychia is 80% or 0.8.

Continuing with our example, let's assume a patient comes into the office and indicates they have redness, but answer no other questions. What is the probability they have paronychia? Using values from the knowledge base we can apply them to our analysis and have the following:

$$p(P|\text{redness}) = \frac{p(P)p(\text{redness}|P)}{p(P)p(\text{redness}|P) + p(\bar{P})p(\text{redness}|\bar{P})}$$

$$p(P|\text{redness}) = \frac{0.6 * 0.8}{0.6 * 0.8 + 0.4 * 0.2}$$

$$p(P|\text{redness}) = 0.86$$

Either the patient has paronychia or they don't. The number in the numerator is computed assuming the patient has paronychia. The numerator is divided by the sum of two numbers, one computed assuming the patient has paronychia (the same one in the numerator) and one computed assuming the patient does not. The probability is therefore, the fraction of that sum that comes from the case in which we assume the patient has the condition. So after seeing that the patient has redness, the probability of having paronychia has jumped from the prior of 0.6 to the posterior of 0.86.

What if we also know that the patient has swelling? The knowledge base indicates that swelling provides a 70% (or 0.7) of paronychia and 30% (or 0.3) that swelling is indicative of another diagnosis. Therefore, the system can determine the probability using two known conditions as:

$$p(P \mid \text{redness, swelling}) = \frac{p(P)p(\text{redness} \mid P)p(\text{swelling} \mid P)}{p(P)p(\text{redness} \mid P)p(\text{swelling} \mid P) +}$$
$$p(\overline{P})p(\text{redness} \mid \overline{P})p(\text{swelling} \mid \overline{P})$$

$$= \frac{0.6 \times 0.8 \times 0.7}{0.6 \times 0.8 \times 0.7 + 0.4 \times 0.2 \times 0.2}$$

$$= 0.95$$

More evidence leads to more certainty about the diagnosis. However, if the patient says the location is somewhere other than the fingertip we see a significant adjustment. Since the knowledge base indicates that p(loc=other|P=yes)=0, and since this term will be included in the numerator of the probability calculation, the probability that the patient has paronychia drops to zero.

Now consider the scenario where the existence of felon as a diagnosis is present. Some of the parameters for the felon condition include pain having an 80% probability with injury having a 70% probability. Suppose the patient complains of pain and injury. What is the probability of felon?

$$p(F \mid \text{pain, injury}) = \frac{p(F)p(\text{pain} \mid F)p(\text{injury} \mid F)}{p(F)p(\text{pain} \mid F)p(\text{injury} \mid F)p}$$
$$(\overline{F})p(\text{pain} \mid \overline{F})p(\text{injury} \mid \overline{F})$$

$$= \frac{0.4 \times 0.8 \times 0.7}{0.4 \times 0.8 \times 0.7 + 0.6 \times 0.2 \times 0.2}$$

$$= 0.90$$

What is the probability of paronychia?

$$p(P \mid \text{pain, injury}) = \frac{p(P)p(\text{pain} \mid P)p(\text{injury} \mid P)}{p(P)p(\text{pain} \mid P)p(\text{injury} \mid P)p}$$
$$(\overline{P})p(\text{pain} \mid \overline{P})p(\text{injury} \mid \overline{P})$$

$$= \frac{0.7 \times 0.6 \times 0.4}{0.7 \times 0.6 \times 0.4 + 0.4 \times 0.2 \times 0.2}$$

$$= 0.91$$

The system now indicates a 90% chance of having one thing and a 91% chance of having another. The system then normalizes by the sum of the probabilities. Thus, the probability of paronychia is 0.91/(0.91+0.90)=0.503 and the probability of felon is 0.90/(0.91+0.90)=0.497. Given this information there is limited reasoning to prefer one over the other. Pain and injury are stronger indicators of felon, but felon has a lower prior probability. In this case, the doctor or care provider may decide more evidence is needed.

In terms of analysis, the preferred embodiment will use the Bayesian method and routine to determine probabilities. Thus, given a disease, D, and a set of symptoms for which we know the patient's state, K={k1, k2, . . . , km} where each $k_i$ is a symptom index, the system will need a routine posterior (D, K) that takes D and K as inputs and outputs the posterior probability of the disease given the symptoms. The system will find the right set of probability tables from the knowledge base using D as an index, and then compute the posterior probability using the indicated symptoms and their observed values via the standard equation:

$$P(D = \text{yes} \mid K) = \frac{p(D = \text{yes})\pi_i p(s_{k_i} \mid D = \text{yes})}{p(D = \text{yes})\pi_i p(s_{k_i} \mid D = \text{yes}) +}$$
$$p(D = \text{no})\pi_i p(s_{k_i} \mid D = \text{no})$$

The system can then display the most probable diseases, or all of the diseases for which the posterior probability is above some threshold, or just the single most probable disease.

In terms of external representations, the system is able to specify the number of values each variable can take on, its parents, and its probability tables. Since the system is configured of one or more software applications resident on one or more computers or servers which handle the calculations and analysis the nomenclature, files, procedures, or calls for performing such functions for paronychia might look like the following:

VAR paronychia
VAR infection
VAR pain
VALUES paronychia T F
VALUES infection T F
VALUES pain T F
PARENTS infection paronychia
PARENTS pain paronychia
PROBABILITY paronychia=T 0.6
PROBABILITY paronychia=F 0.4
PROBABILITY infection=T paronychia=T 0.9
PROBABILITY infection=F paronychia=T 0.1
PROBABILITY infection=T paronychia=F 0.2
PROBABILITY infection=F paronychia=F 0.8
PROBABILITY pain=T paronychia=T 0.7
PROBABILITY pain=F paronychia=T 0.3
PROBABILITY pain=T paronychia=F 0.2
PROBABILITY pain=F paronychia=F 0.8

The VAR statements name variables. The VALUES statements take a variable as the first argument followed by a list of possible values for the named variable. The PARENTS statements take a variable as the first argument followed by one or more variables that are its parents in the BN. The PROBABILITY statements take a variable/value pair as the first argument, a list of variable/value pairs after that, and a real value last. The first variable/value pair is the variable for which the probability is specified, and the other variable/value pairs specify a state of the parents.

As described above, for symptoms $s_1$-$s_n$ and disease D, the probability of the disease given the symptoms can be computed as follows:

$$p(D \mid s_1, s_2, \ldots, s_n) = \frac{p(D)\pi_i p(s_{k_i} \mid D)}{p(D)\pi_i p(s_{s_i} \mid D) + p(\overline{D})\pi_i p(s_i \mid \overline{D})}$$

In the above equation, p(D) is the prior probability of having the disease, p($\overline{D}$) is the prior probability of not having the disease, p($s_i$|D) is the probability the patient has symptom $s_i$ given that they have the disease, and p($s_i$|$\overline{D}$) is the probability the patient has the symptom given that they do not have the disease. The system obtains p(D), p($\overline{D}$), and p($s_i$|D) from patient information, analysis or from the knowledge base. Rather than computing p(D|$s_1$, $s_2$, . . . , $s_n$) and p($\overline{D}$|$s_1$, $s_2$, . . . , $s_n$) for each disease D, the system can use a random variable, (i.e. V), that takes values from the set of all diseases. Suppose, for the sake of an example, that this set is paronychia, felon, and carpal tunnel (ct). Then the expression p(felon|$s_1$, $s_2$, . . . , $s_n$) becomes:

$$p(\text{felon} | s_1, s_2, \ldots, s_n) = \frac{p(\text{felon})\pi_i p(s_i | \text{felon})}{\begin{array}{l} p(\text{felon})\pi_i p(s_i | \text{felon}) + \\ p(\text{paronychia})\pi_i p(s_i | \text{paronychia}) + \\ p(ct)\pi_i p(s_i | ct) \end{array}}$$

The only change is that the system can decompose the absence of the disease into the sum of all of the things that it could be other than felon and obviates the need to compute probabilities conditioned on $\overline{D}$ for any D∈V.

The reasoning can also be applied to learning the diagnosis. Suppose the system indicates based on probability calculations that the patient has felon but the doctor chooses paronychia. The system is able to move the baseline/Bayesian network in the direction of choosing paronychia in the future by addition or counting. For example, to estimate p(felon) the system counts how many patients had felon or felon patients (FP) and how many total patients (TP) have been seen and computes the ratio: p(felon)=FP/TP. To estimate $p(s_i|D)$ you divide the number of people who had the symptom and the disease by the number of people who had the disease. The system can update these probabilities as new patients are seen.

Suppose FP and TP are as defined above. Each time a patient comes to the office for a new problem you increment TP by 1. Each time such a patient is diagnosed with felon you increment FP by 1. Note that the magnitudes of FP and b are important in determining how much such a new patient will change p(felon). If FP=1 and TP=2 then p(felon)=FP/TP=1/2=0.5. A new patient with felon results in p(felon)=FP/TP=2/3=0.67.

However, if FP=100 and TP=200 then p(felon)=0.5 as before, but a new patient with felon changes this probability by only a small amount: p(felon)=FP/TP=101/201=0.502. When a patient comes in with a set of symptoms and is given a diagnosis by the doctor, the system can do the following: (1) increment the total patient count and the count of the number of patients given that diagnosis by 1; and (2) for each symptom the patient reported, increment the count of the number of patients who both reported that symptom and received the diagnosis by 1. By implementing such rules, the system causes the prior probability of that diagnosis to increase and that of the other, competing diagnoses to decrease while also increasing the $p(s_i|D)$ for each symptom.

The net effect makes the given diagnosis more likely (by the Bayesian Network) in similar situations in the future. Note that if the system incremented the counts by 2 instead of 1, it is as if we had seen 2 patients with the same symptoms and diagnosis and $p(D|s_1, s_2, \ldots s_n)$ will be even larger.

The system can increment the counts by any number an administrator would like to use. However, the larger the increment, the greater the impact on the posterior probability of the diagnosis given the disease. Recall that the impact on the posterior is a function of both the size of the increment and the current counts. For a fixed increment, the effect is larger for smaller current counts.

Thus, to control the rate at which the system adapts, the system only needs to alter the size of the update performed each time the doctor makes or selects, a diagnosis. For example, the system could have a system parameter, which takes on values from 1 to 100. Each time a patient is diagnosed, the counts are updated by the system parameter. The larger system parameter the faster the system will adapt to match what the doctor does as opposed to the baseline of the knowledge base.

The system also employs a similar methodology for learning the care provider profile for treatment plans. As described above, each treatment plan has an established baseline probabilities resident in the knowledge base. For example, there might be 4 groups of things that are performed for patients that have felon, and there is some probability of choosing each of the four. Within the four groups, there may be probabilities for each component of a group. The system can update the priors on each group by seeing what the doctor chooses for a patient, and likewise for the components of each group. Again, a factor can be used to control how quickly the system adapts to response differences between what the system (or baseline) provides and what the doctor decides.

An example of the present invention in use will now be described in conjunction with FIGS. 8-23 which depict access to the features and functionality through various graphical user interfaces or screens.

Figure 8:
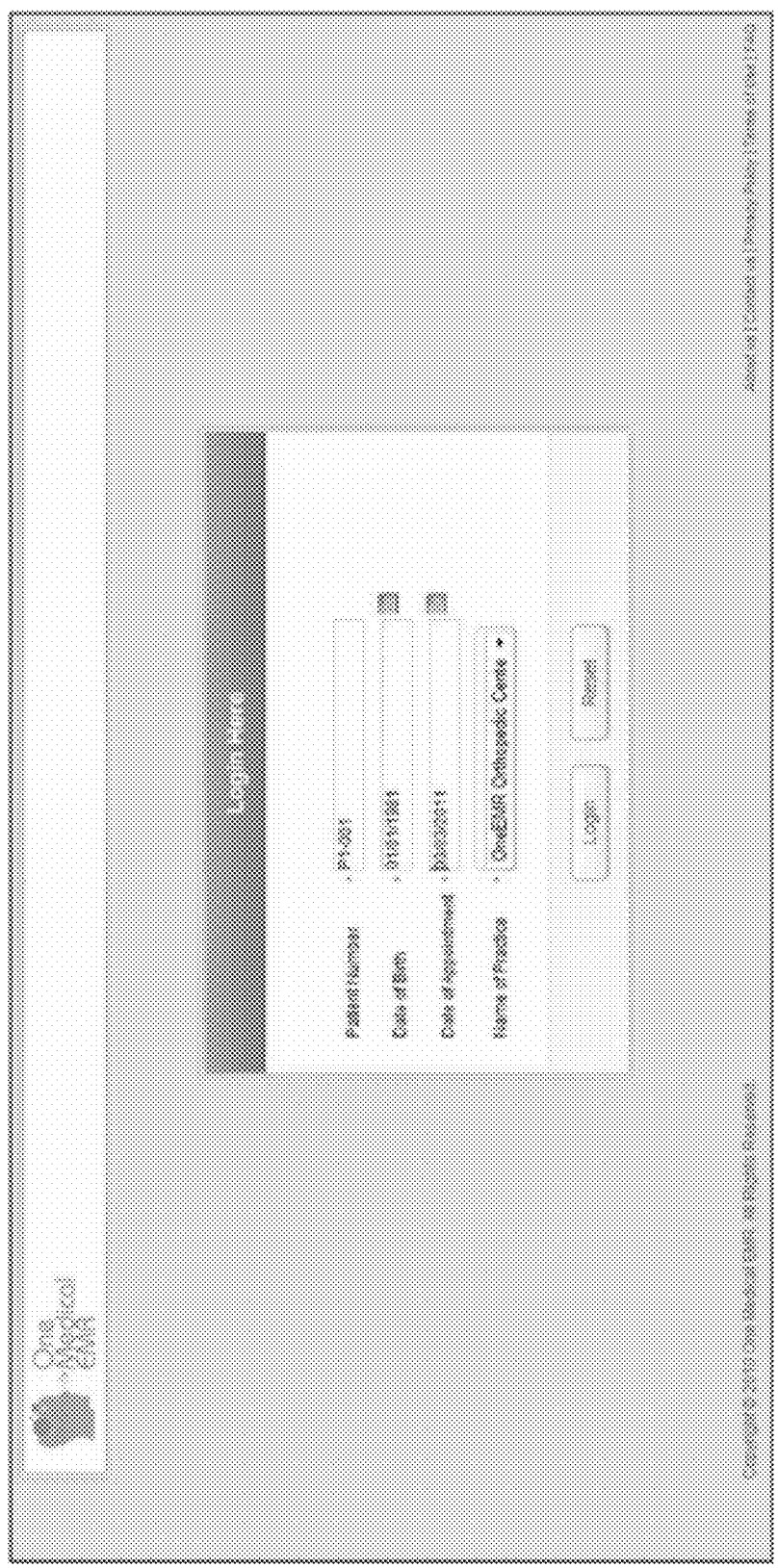

FIG. 8 depicts a login screen or graphical user interface 800. The system login may have the same or different login screens for the various users. Those users would include patients, medical assistants, doctors, medical practice administrative assistants, billing assistants, lab workers and technicians and any other logical party that would need and is allowed access to the system or information. The system enables each of the users to have an identified administrative role which grants or limits access to what information they can see, review, edit, and add. In our example, a patient will use login screen 800 to login at the kiosk at the doctor's office. The Login interface 800 may include information fields such as patient number, date of birth, date of appointment, name of practice and other patient related fields.

Figure 9:
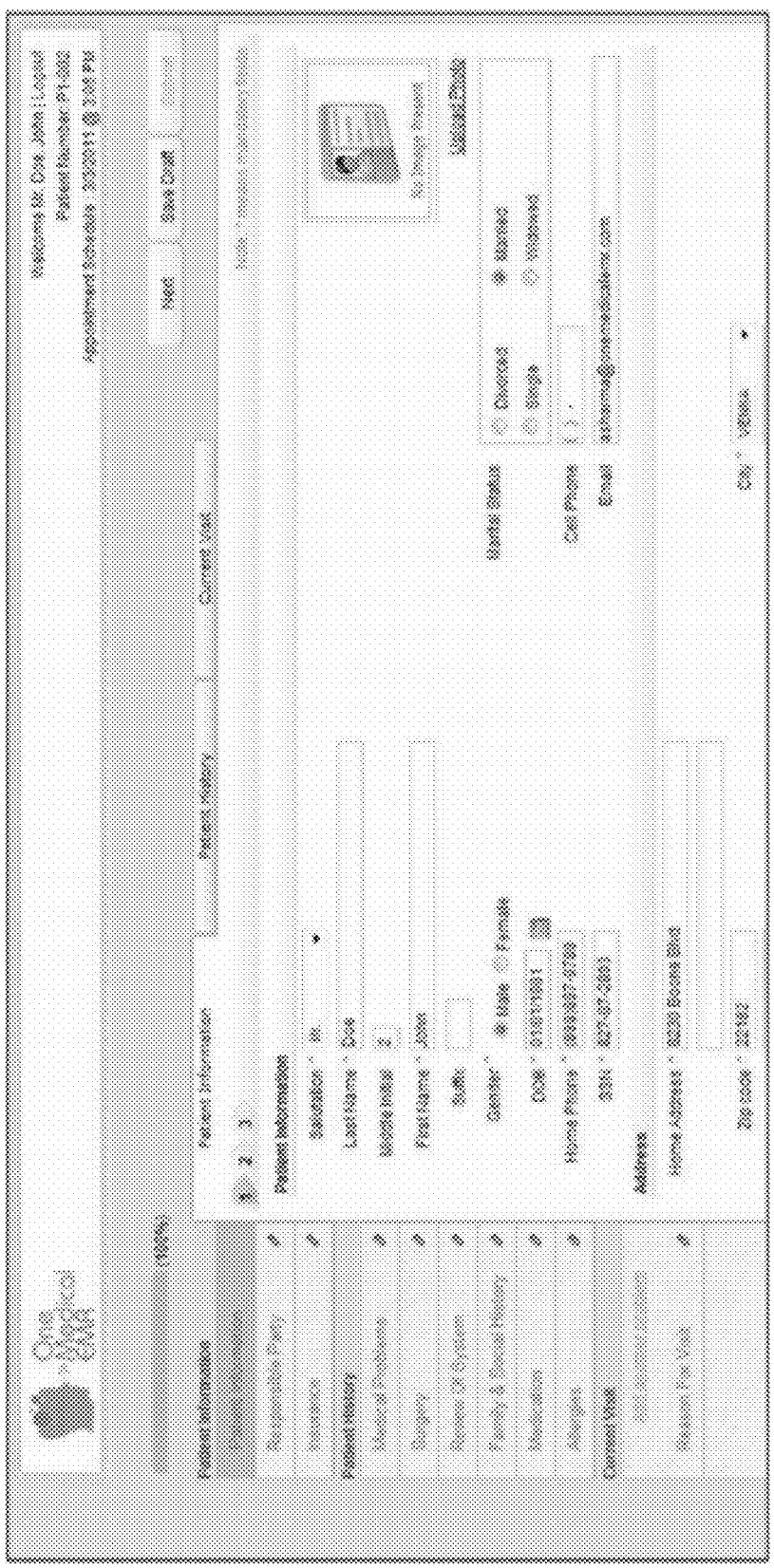

The patient, after logging into the system, is presented a series of screens or graphic user interfaces, as depicted in FIGS. 9-16, for reviewing, adding, or editing various pieces of information. As seen in FIG. 9, user interface 900 provides an interface for the patient to provide or edit patient information. The patient information would include standard fields including name, address, phone, email, date of birth, social security number, insurance information and other logical patient information. The Patient Information display 900 may include name, address, phone, social security number, date of birth, gender, email, and other fields along with tabs for patient history and current visit.

Figure 10:
Figure 11:
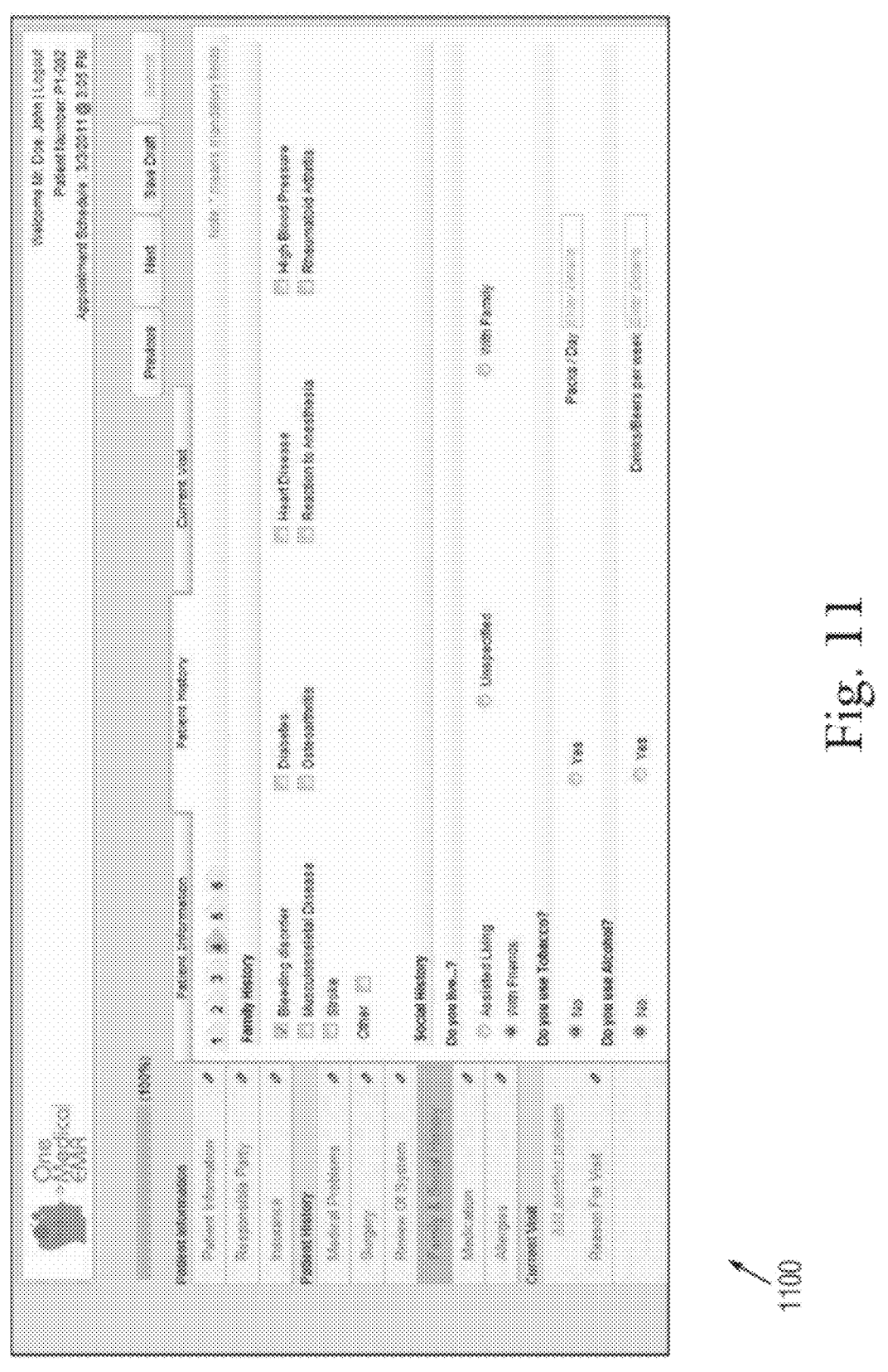
Figure 12:
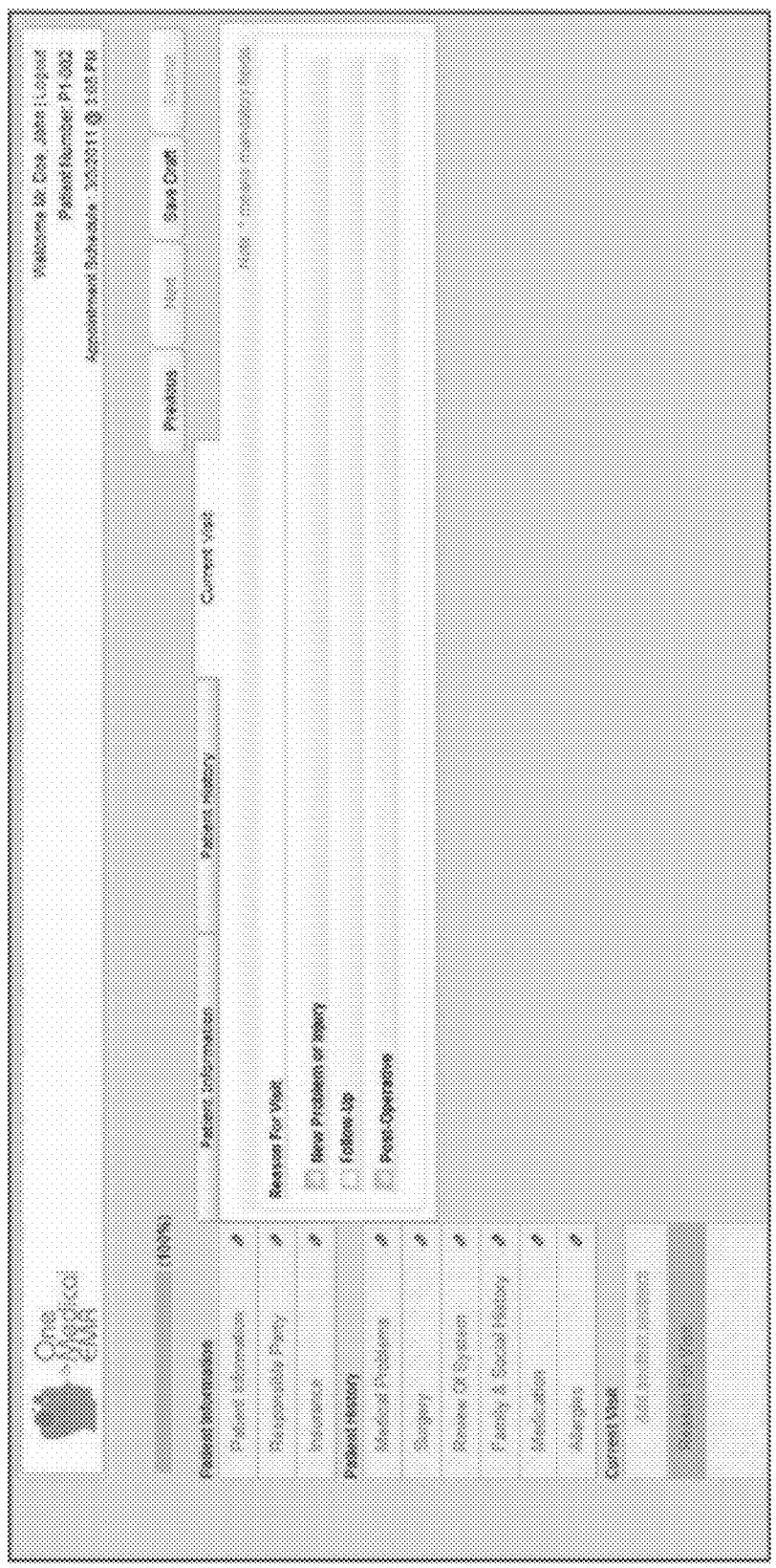
Figure 13:
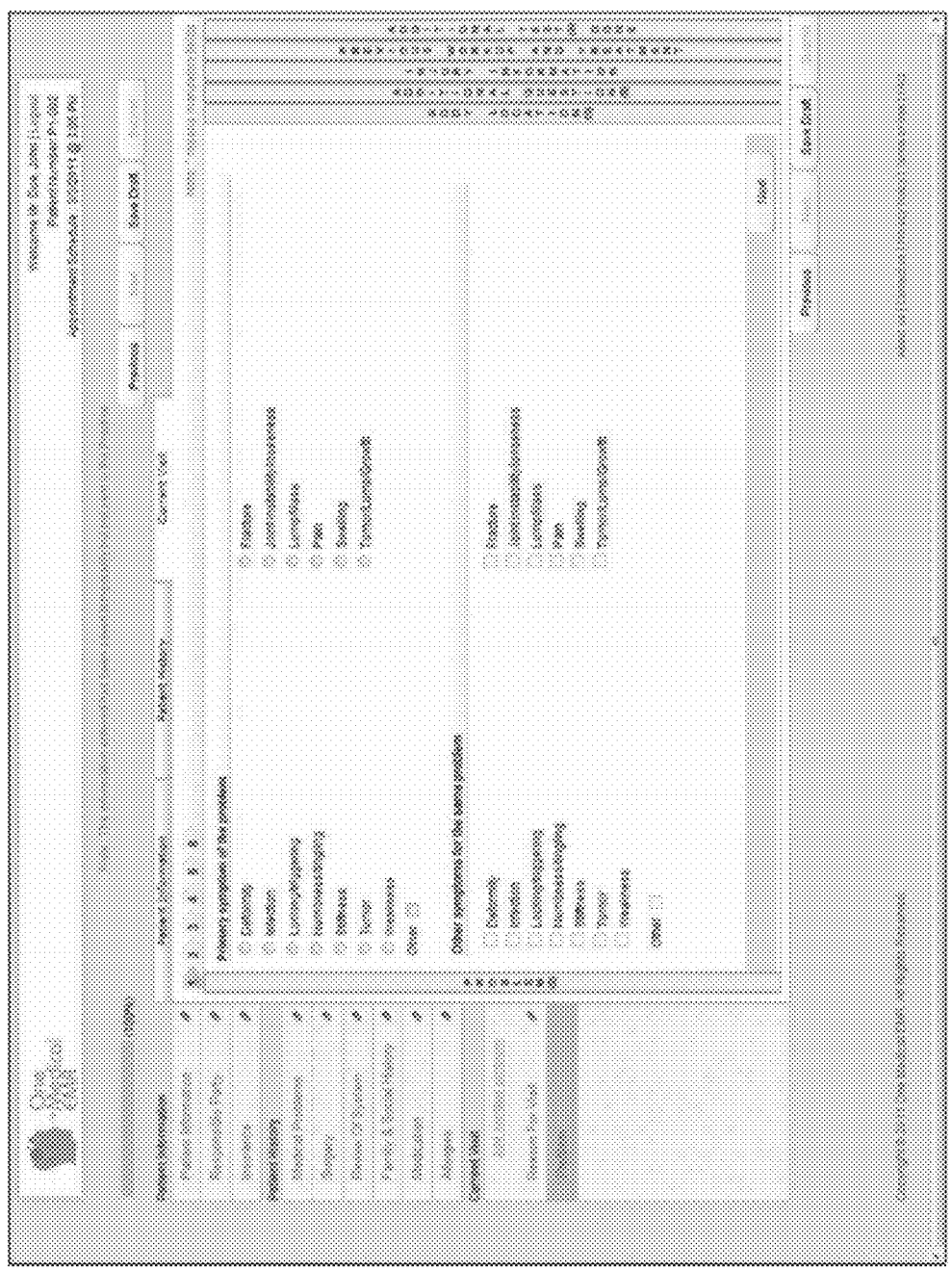
Figure 14:
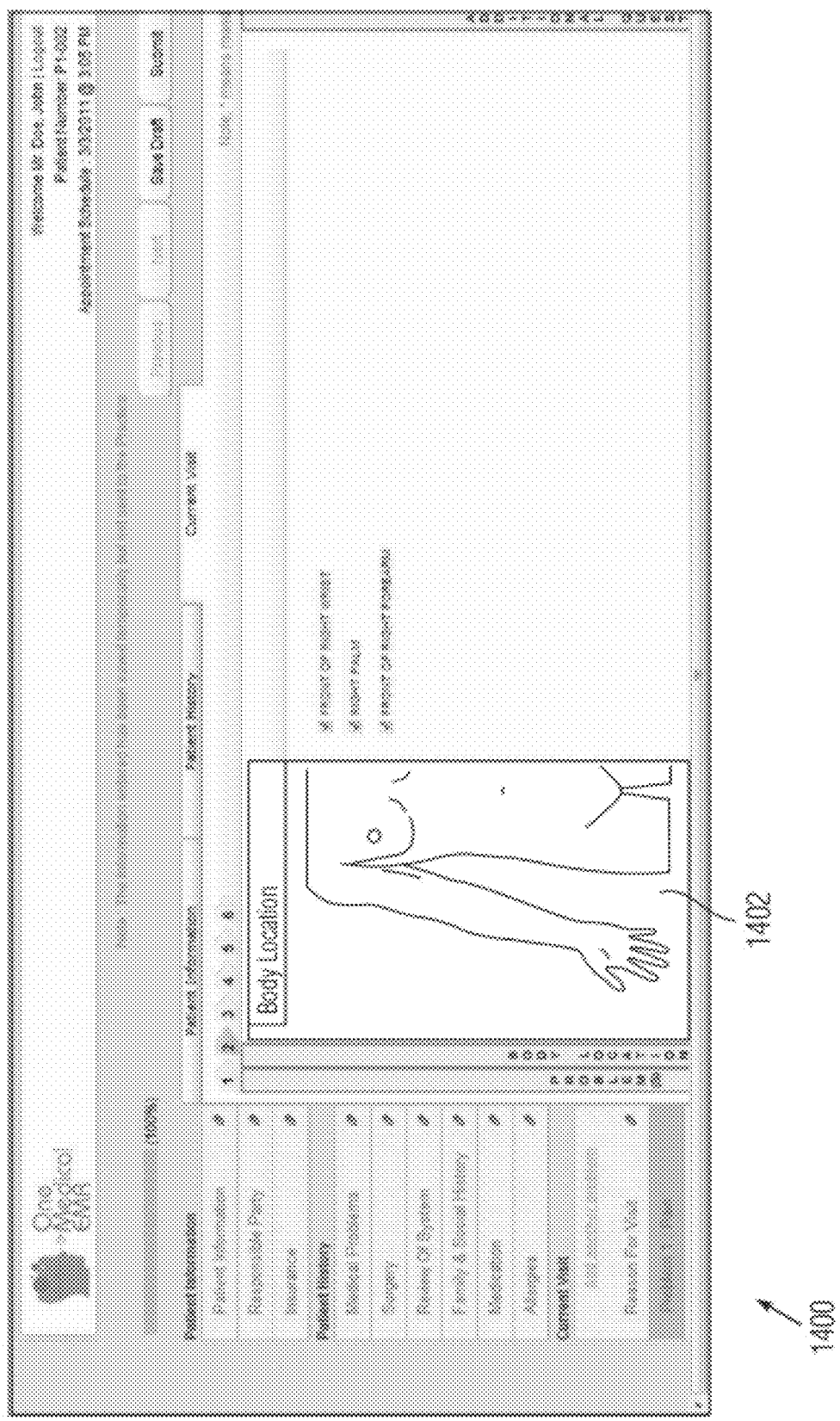
Figure 15:
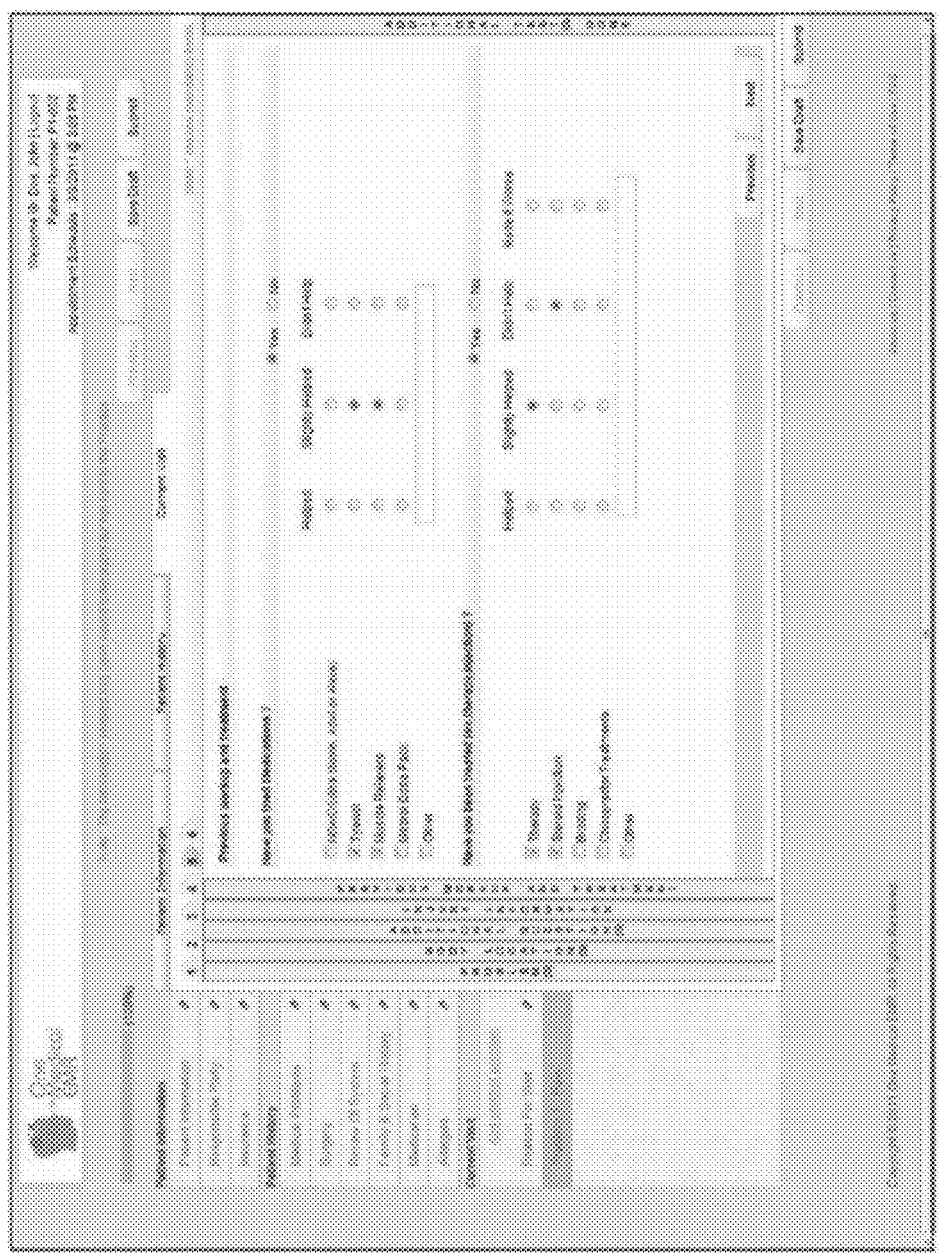
Figure 16:
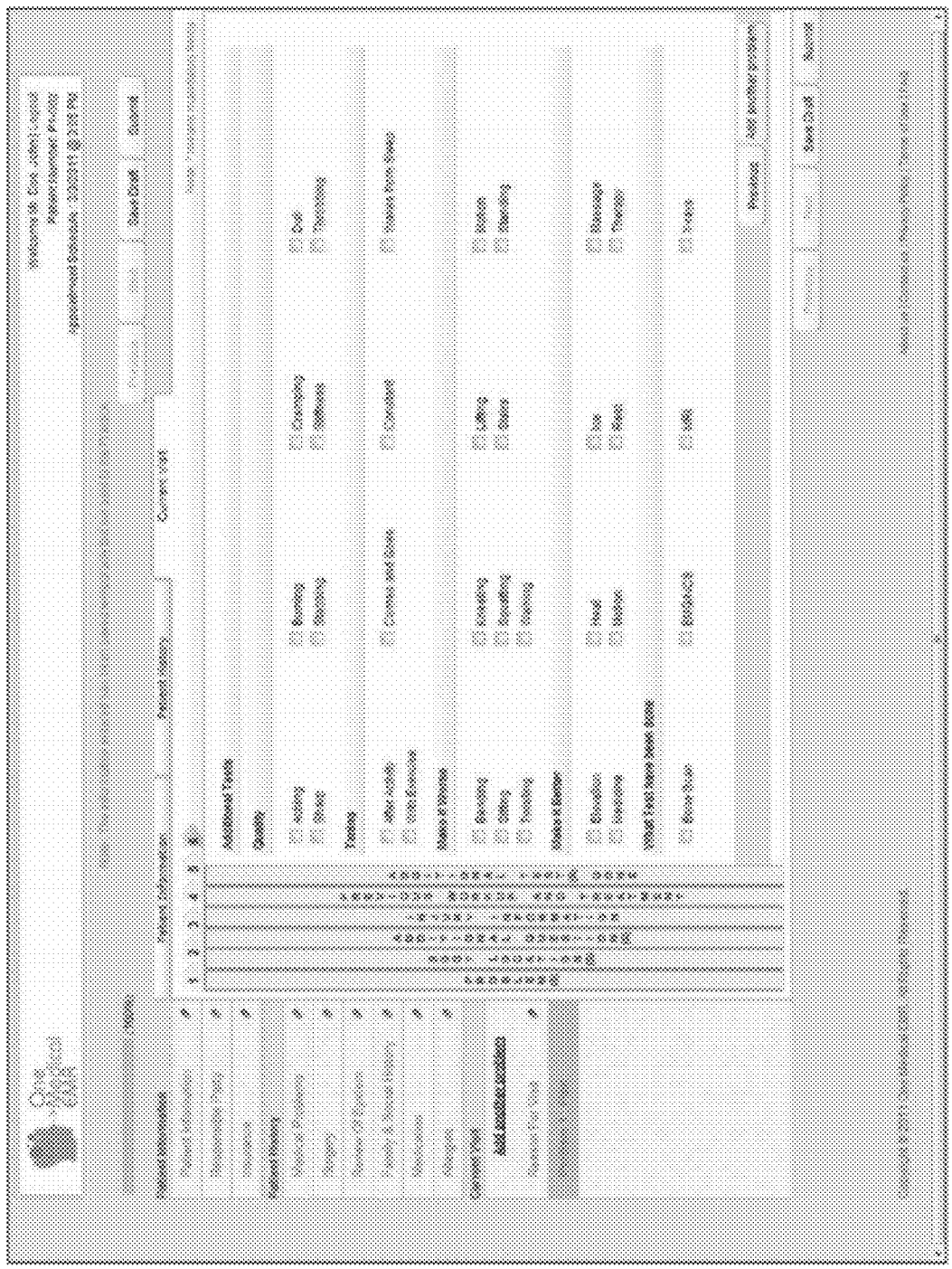

As seen in FIGS. 10 and 11, the patient is provided a user interface 1000 and 1100 for providing patient historical information. As seen on interface 1000 the patient may input and review past medical problems. On interface 1100 the patient may provide additional family history and social history information. In the preferred embodiment, the patient reviews and enters the information directly. However, an administrative or medical assistant can enter the information for the patient. After the various patient and history information is reviewed and entered into the system the patient provides information on the reasons for their current visit.

As seen in FIGS. 12-16, the patient is provided a series of screens or user interfaces 1200, 1300, 1400, 1500, 1600 for providing information specific to the current visit. On interface 1200 the user identifies if there is a new problem of injury. In our example, our patient has a new problem related to a lump or mass with pain near his wrist. On interface 1300 the user can identify the primary symptom and other symptoms. On interface 1400, the user interacts with a series of interactive images as viewed in window 1402. Through the images in the window 1402, the user clicks on or selects the area related to the problem. As our example continues, the patient has identified the area as the front of the right wrist, palm, and forearm.

On screen 1500 the patient can provide information on whether certain medications of treatments have been beneficial in treating the pain. On screen 1600 a series of additional questions may be presented to the patient to help the system and doctor more accurately identify an appropriate diagnosis. The user interface screens depicted in FIGS. 8-16 are examples of several interfaces which can be employed but are clearly not intended to limit the number and types of interfaces which could be employed by the system to enable the patient or an assistant to enter information related to the patient or problem.

Once the information has been entered, the system then uses the information and responses to questions and analyzes the data against one or more knowledgebase sets. Through the analytical analysis the system generates a list of potential diagnoses based on probability. The calculated probabilities are then used to rank and list the potential diagnosis for use by the medical practice doctors and medical assistants.

Figure 17:
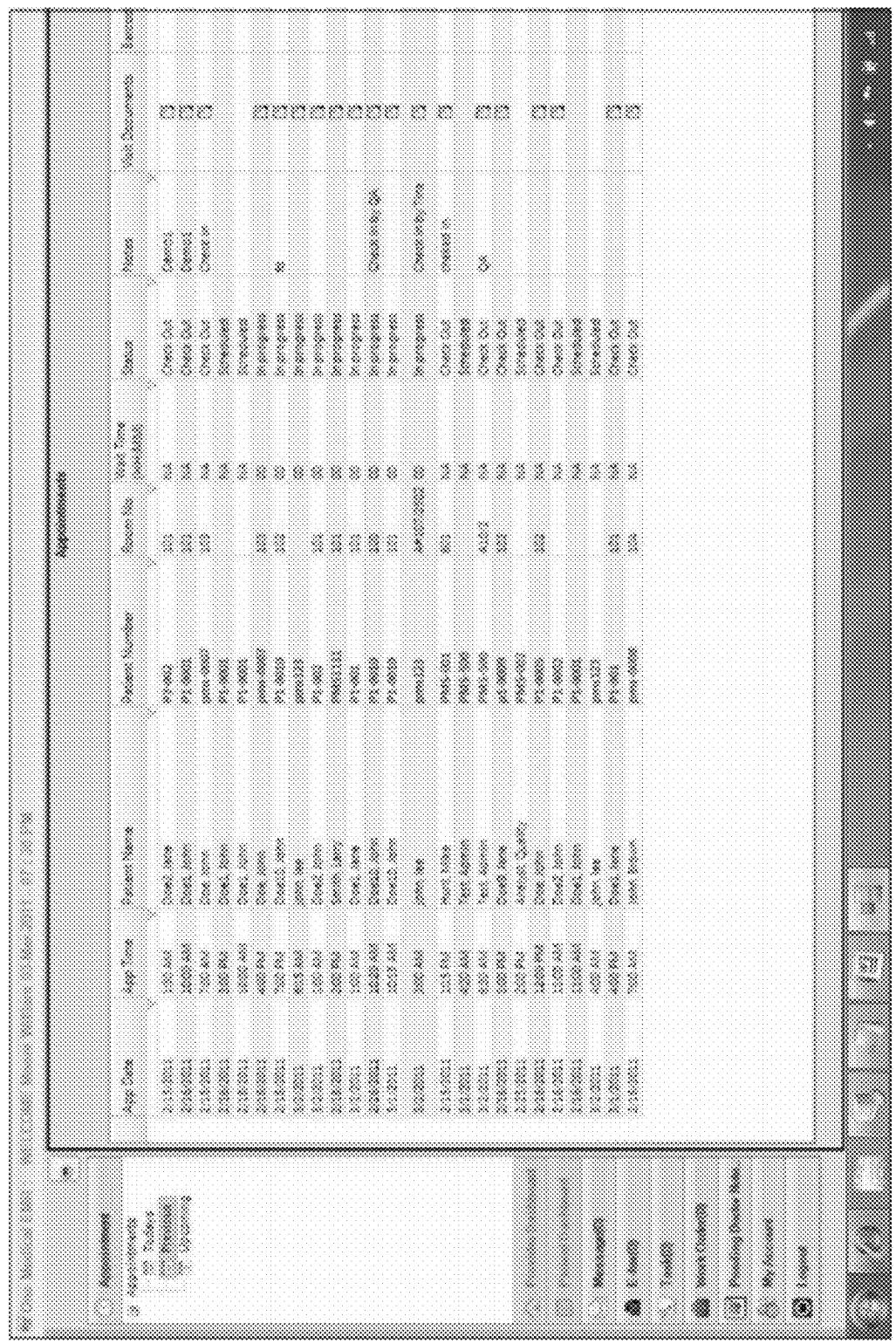

As seen in FIG. 17, when a doctor or medical assistant logs into the system they are provided one or more user interfaces 1700 where they can view scheduled appointments, previous appointments or upcoming appointments. By selecting one of the patients or files from screen 1700 the doctor is presented with all pertinent information of the patient and can view their historical health information as well as the reasons for their current visit. Thus the system enables the doctor to review information already on the patients EMR as well as the specific reasons and information on the purpose of the scheduled appointment. Further, the system can display to the doctor a potential diagnosis to list of diagnoses.

Figure 18:
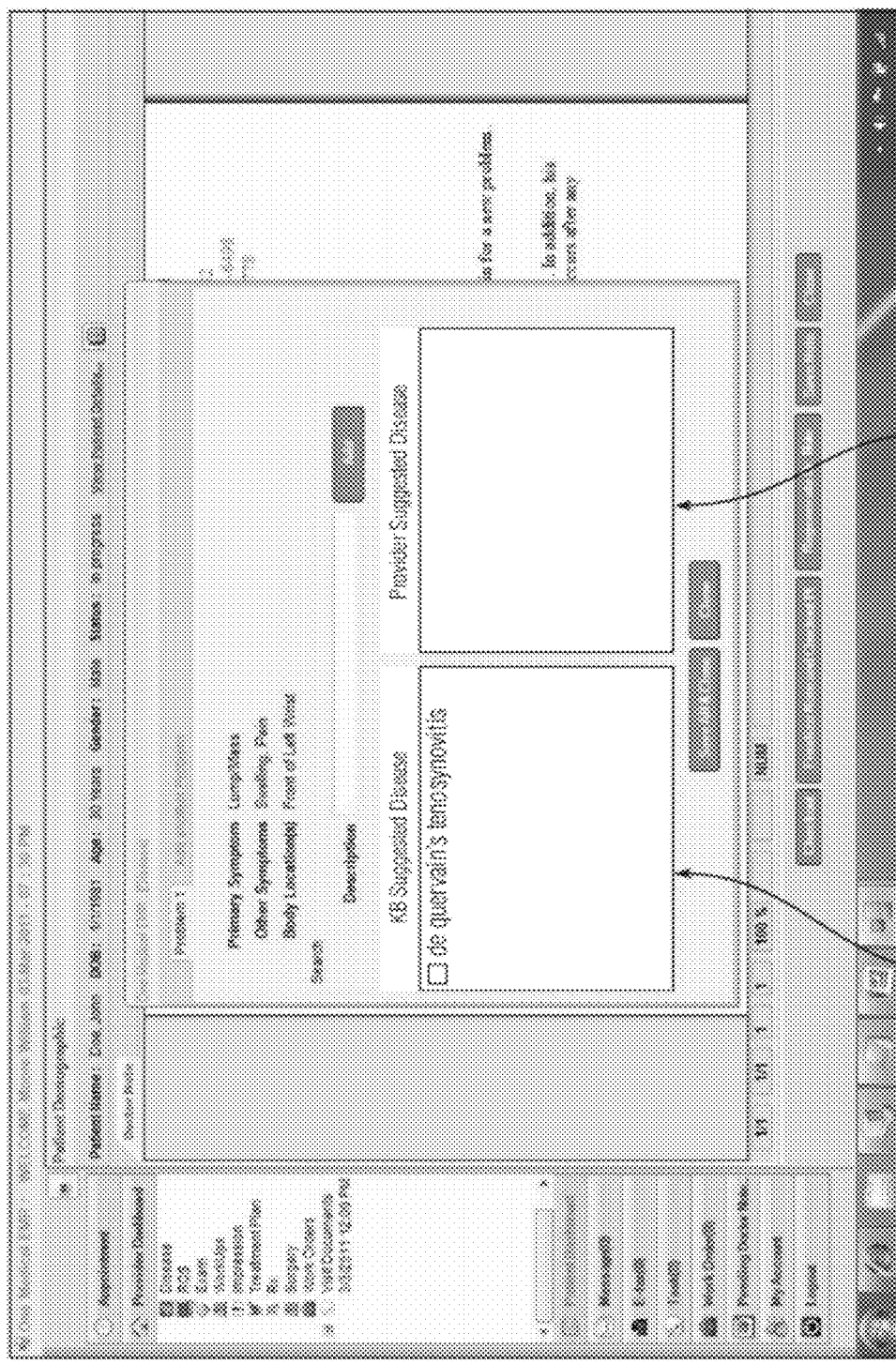

As seen in FIG. 18, the doctor is presented with a user interface 1800 which provides a window 1802 which lists the suggested disease or diagnosis based upon the knowledgebase. The doctor may select the suggested diagnosis or may add a suggested disease or diagnosis which will then be displayed in the provider suggested disease window 1804.

Figure 19:
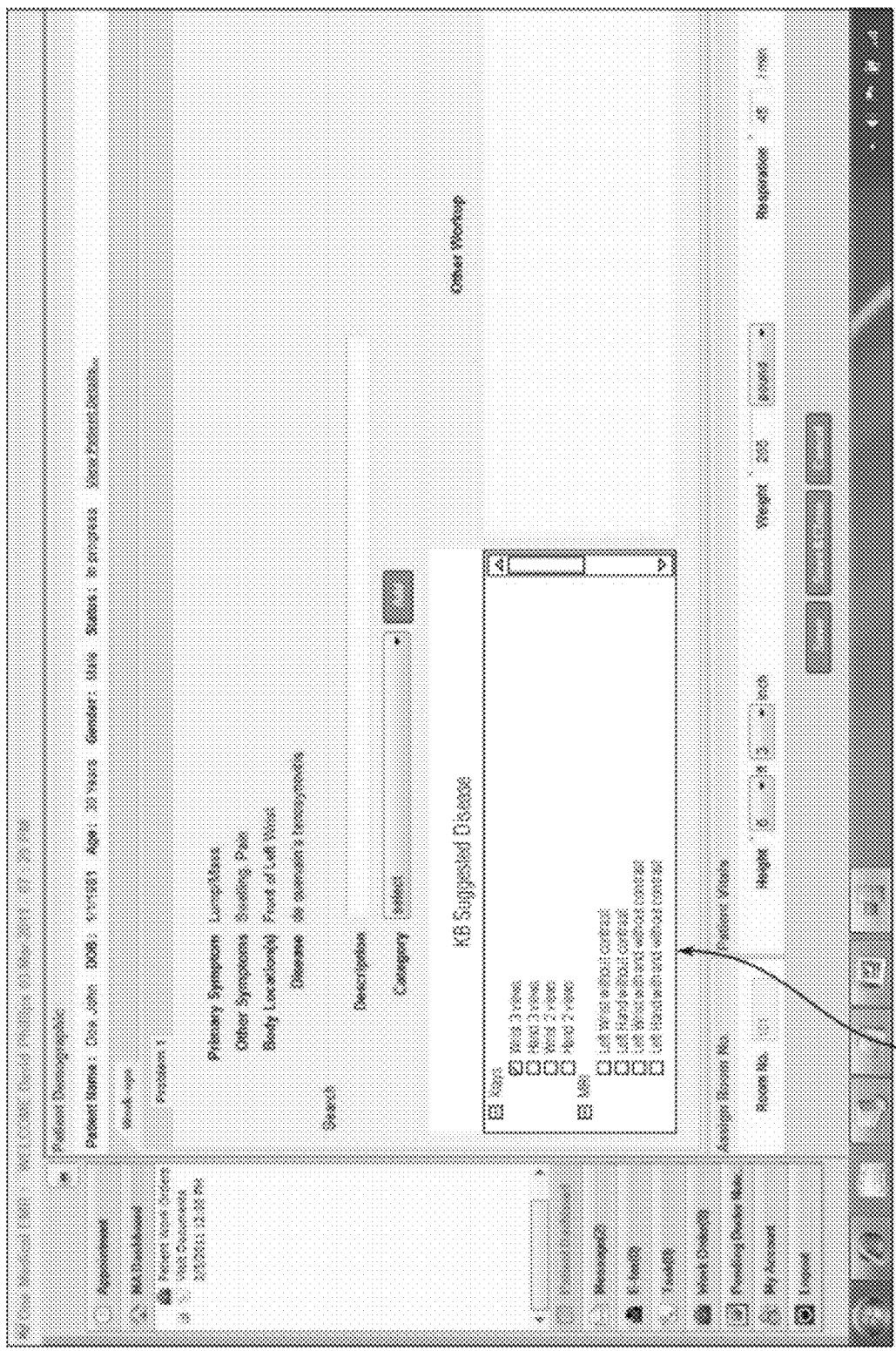

Once the doctor selects or approves the diagnosis, the system analyzes the knowledgebase and the doctor's preferences to determine and provide the suggested workup. As seen in FIG. 19, the doctor is provided a graphical user interface screen 1900 which indicates various tests which the doctor selects or approves. The activities most likely to be selected such as the various tests, procedures, medications or other response may be activity may be pre-checked and are merely seeking the doctor's approval or confirmation.

For our example, based on the patients lump/mass and swelling and pain in the wrist, the system suggested to the doctor in screen 1800 that the patient may have "de quervain's tenosynovitis." On interface 1900 the system indicates that a 3 view X-ray of the wrist is suggested as one of the workup procedures.

Figure 20:
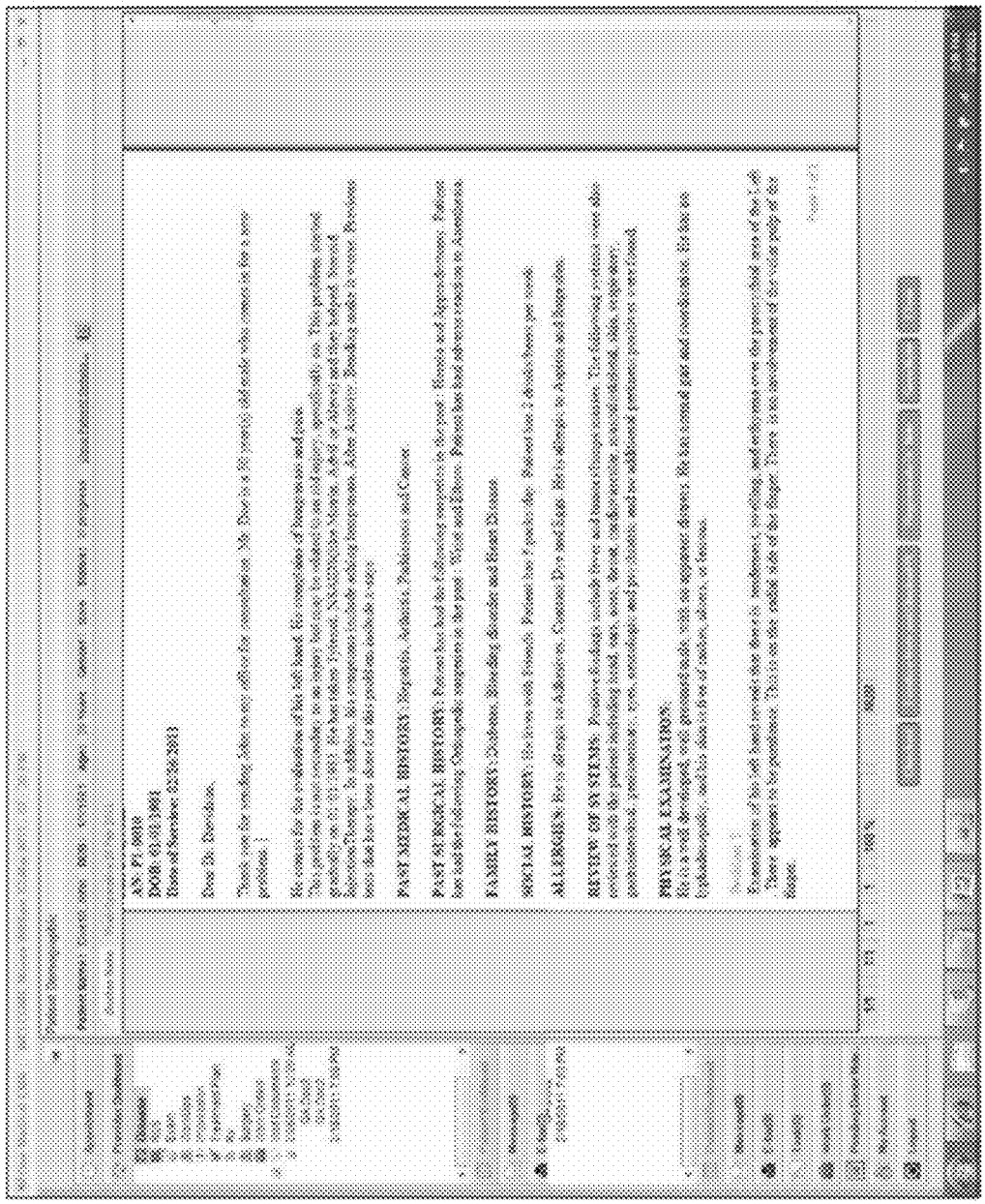

Another important aspect of the present invention is the ability of the system to generate the Doctor's Note upon completion of the examination and planned method of treatment. As seen in FIG. 20, after selection of the diagnosis and treatment, the system generates the various workup orders and the doctor's note are displayed on interface 2000. The doctor's note includes pre generated letters to referring doctors, notes to lab technicians for tests to be performed, and any other logical step. The doctor may edit the note directly prior to finalizing the note and checking out the patient.

Figure 21:
Figure 22:
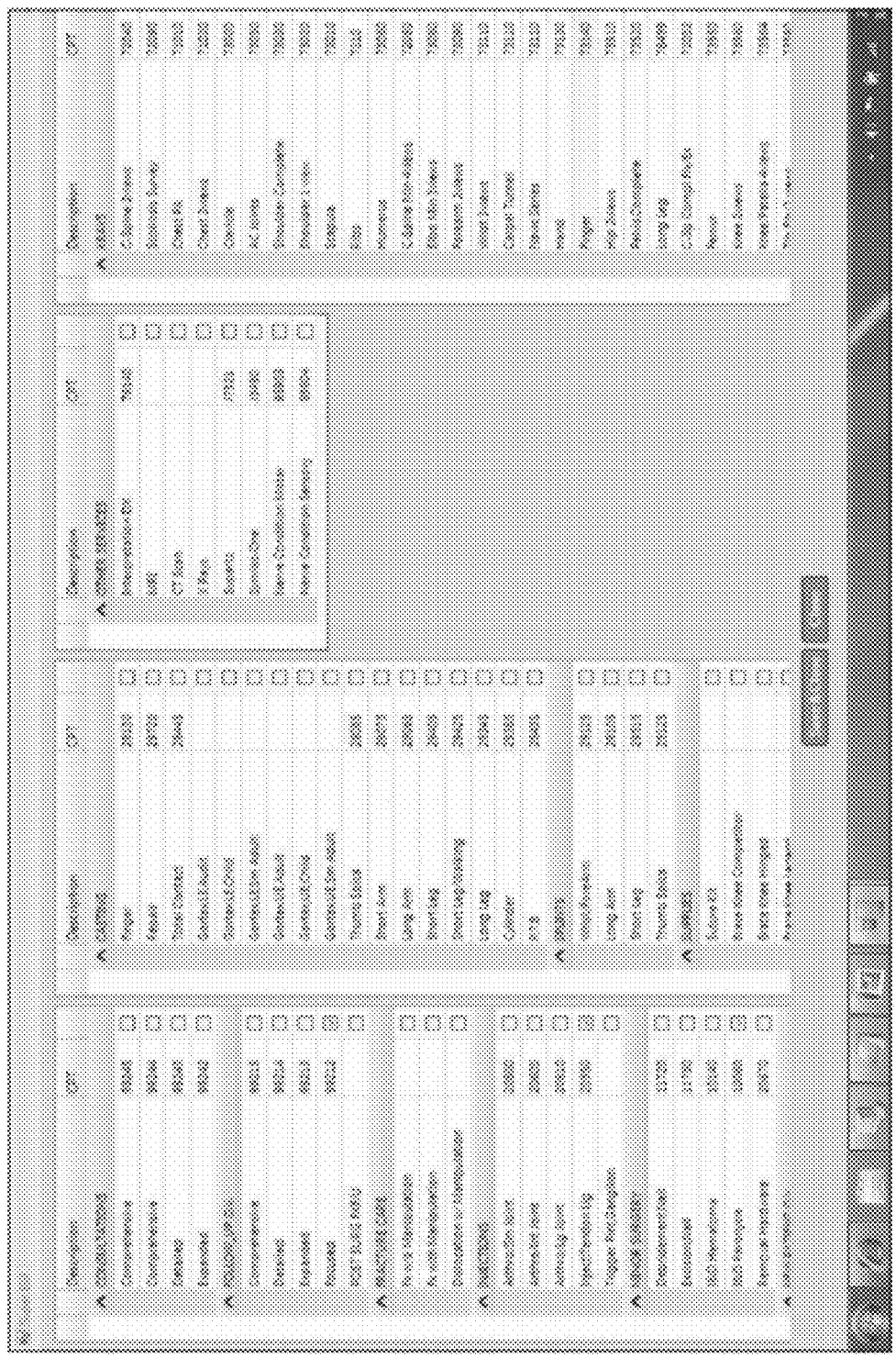
Figure 23:
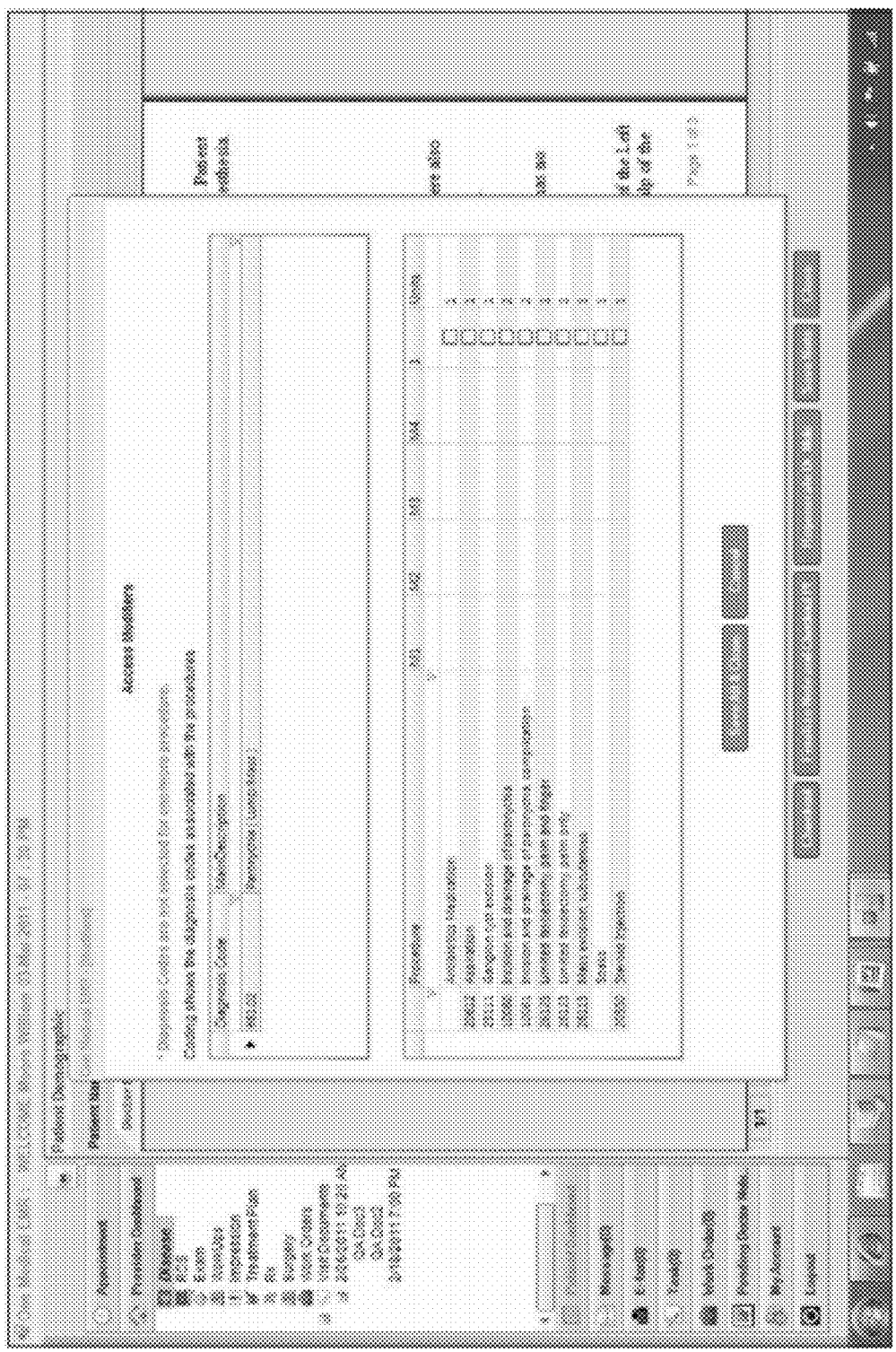

Once the note has been finalized, the system generates all of the orders and determines all of the appropriate CPT codes and billing information. As seen in FIG. 21 on interface 2100, the system provides a detailed view of all pending work orders. However, the system also tracks work orders in process, those completed and enables users to identify overdue orders. As seen in FIG. 22 on interface 2200, the system further provides an electronic routing slip with appropriate CPT codes which can be used by the medical practice to route the patient and work orders to the various departments for proper processing. FIG. 23 provides a screen capture 2300 of the various work order procedures required to be performed for use in appropriate billing systems. By tracking the CPT codes throughout the process, the system can automatically generate the information needed for submission to insurance and the client for payment.

As previously discussed, the system can use various analytical methodologies to determine or estimate the probability that a diagnosis is true. In the preferred embodiment, the system will use a Bayesian methodology such that it will use an iterative process in which the collection of new evidence repeatedly modifies an initial confidence in a determined probability of a diagnosis. The system has the ability to apply this reasoning in various aspects and analysis. The system can use new data on the diagnosis and treatment plans selected by a specific doctor to modify and learn that doctor's preferences on both diagnosis and treatment. The system can also collectively use the data of all or a subset of doctors to repeatedly modify the baseline Knowledge Base recommendations for diagnosis and treatments. Further, the system can use a subset of data specific to time or location to repeatedly modify the baseline Knowledge Base recommendations for diagnosis and treatments or to modify a doctor's preferences. Such functionality is useful in instances where diagnosis may change with seasonal differences or where the KB identifies an increased diagnosis of a certain illness within a certain location and can increase the probability of such an illness (such as during a flu outbreak).

As the doctor begins using the system the doctor has the option of using the baseline of the knowledge base of the system or may choose not to start with a baseline. If the doctor does not use a baseline then the system will not make any diagnosis recommendations until the doctor has started entering diagnosis for patients. The data related to the patients and the doctors diagnosis and treatments are added to build that doctor's specific knowledge base. As the doctor sees more patients, the data and symptoms of new patients are then analyzed against that specific doctor's knowledge base and the system determines the probability of diagnosis and present such to the doctor as described above.

In the preferred embodiment, if the doctor uses the system baseline knowledge base, the doctor is presented with list at least the three (3) diagnoses. Each diagnoses is associated with a preset probability value given the patient, provider, and practice factors. An example would be a probability like 7 out of 10 or (0.7). When the doctor selects a diagnosis, the system then incrementally changes the weights by some amount (i.e., add 0.01) of these factors so to increase the probability this diagnosis is predicted in the future if similar factors are encountered. For all unselected diagnoses, the system can incrementally decrease the weights by some amount (i.e. subtract 0.01). For example, when the doctor does not select the $1^{st}$ diagnosis but selects an alternative diagnosis ($2^{nd}$ diagnosis), the system will still increase the weights associated with the selection of the $2^{nd}$ diagnosis. Thus, the system not only has the option of increasing weights for a selected diagnosis but also decreasing weights for the non-selected diagnoses. The doctors also have the ability to control the weighting factor such that their decisions can have a much more immediate impact such as by adding or subtracting a higher number (i.e. 0.05) to the probability score. In addition, doctors can establish filters which limit the number of diagnosis presented to only those above a threshold value. For example, the doctor may only want to have diagnosis with a probability above 0.5 or 50% displayed. As more are patients seen and more data and symptom scenarios are added the system builds an adjusted knowledge base engine for each doctor factoring in that doctor's preferences and historical diagnosis decisions.

The system also learns the doctor's preference on treatments and treatment plans including tests, medications, therapy, and consults. Again the doctor may choose to use the system's baseline treatment plan or build their own baseline by informing the system of preferred or prescribed treatment plans. Again, the system will track any modifications to the baseline and adjust accordingly or will build a baseline if the practitioner started without use of the system baseline. The doctor may create their own treatment plans which are pre-installed into the system prior to seeing patients.

Another major benefit of the present invention is the ability for the system to adjust the suggested treatment plans based on patient specific factors. Such factors might include insurance approvals, allergies to specific medications, medication recalls, and other factors. Since the system allows the medical practice to apply rules and logic to the treatment plans based on many factors the system can recommend alternative treatment plans for patients with the same diagnosis but different insurance or other factors. The system can also narrow or tailor or filter the knowledge base to doctors within a specific region (for example, the state of Maryland) to determine the optimal treatment plans based on what other doctors in that region are prescribing with patients with similar insurance and health concerns. The doctors may also choose to have some diagnosis use the knowledge base suggested treatment plans while other diagnosis use a doctor defined treatment plan or no pre-set treatment plan.

Another aspect of the present invention is the alert or notification component. As described herein, based on the diagnosis the doctor's preferences with regards to treatment plans through the baseline plan, adjusted and learned baseline, predefined plan, or no set plan various work orders are generated for treatment plans, tests, medications and the like. The notification component is able to alert and notify the various constituents in the patient life cycle of tasks needed to be conducted as well as notification of completion of those tasks. Such notifications can be used to automatically schedule appointments such as appointment for an x-ray and follow-up appointments once the x-rays are available for doctor review. The alerts and notifications can also be used by the medical practice groups to manage resources.

Another important aspect of the present invention is the ability for the system to allow for the creation of text into the Doctor's Note through the provider's voice. One way is to allow the recording of the provider's voice into audio files. These audio files are referenced by patient, provider, date of service, and location with the Doctor's Note. The audio file that can be transcribed into text by an outside medical transcriptionist or outside voice recognition software and be automatically inserted back into the Doctor's Note. The second way is through the use or integration of voice recognition software such as Dragon Naturally Speaking Medical. This system enables doctors to dictate additions/modifications to a doctor's note and get immediate voice to text translation directly into the Doctor's Note. Thus, a doctor can quickly input and finalize the note for more efficient patient processing, and to allow for more time for actual treatment of patients.

The system also enables doctors to generate surgical work orders which can be set to automatically trigger various rules including scheduling surgical room time, anesthesiologists and other factors. The system may also be integrated with digital prescription systems such that a patient's preferred pharmacy can be notified of a prescription that need to be filled automatically. This can also be useful in tracking current medications that a patient may be taking to avoid medicinal conflicts. The system has the ability to interact with the digital prescriptions standards as well and integrate all data back to the patients EMR.

The foregoing examples have been provided merely for the purpose of explanation and are in no way to be construed as limiting of the present method and product disclosed herein. While the invention has been described with reference to various embodiments, it is understood that the words which have been used herein are words of description and illustration, rather than words of limitation. Further, although the invention has been described herein with reference to particular means, materials, and embodiments, the invention is not intended to be limited to the particulars disclosed herein; rather, the invention expands to all functionally equivalent structures, methods and uses, such as are within the scope of the appended claims. Those skilled in the art, having the benefit of the teachings of this specification, may affect numerous modifications thereto and changes may be made without departing from the scope and spirit of the invention in its aspects.

It will be recognized by those skilled in the art that changes or modifications may be made to the above described embodiment without departing from the broad inventive concepts of the invention. It is understood therefore that the invention is not limited to the particular embodiment which is described, but is intended to cover all modifications and changes within the scope and spirit of the invention.

What is claimed is:

1. An intelligent care provider medical practice system comprising:
    at least one server;
    at least one client computer in communication with the at least one server;
    at least one database in communication with the at least one server, wherein the at least one database has at least one medical knowledge base;
    at least one software application resident on the server, wherein the system provides:
        a graphical user interface on the at least one client computer configured to allow entry of a plurality of patient information and at least one patient health problem;
        a comparative analysis of the plurality of patient information and at least one patient health problem with the at least one medical knowledge base to identify one or more diagnosis;
        a calculation of the probability of each of the identified at least one diagnosis based upon the comparative analysis;
        an adjustment of the calculated probabilities based upon a care provider diagnosis profile, wherein the care provider diagnosis profile is a learned diagnosis profile based upon at least one previously selected diagnosis and at least one previously presented diagnosis which was not selected; and
        ranking the diagnoses based on the adjusted calculated probability.

2. The system of claim 1, wherein the system receives a selection of one of the plurality of ranked diagnosis from the care provide using one of the at least one client computer.

3. The system of claim 2, wherein upon receipt of the selected diagnosis, the at least one software application generates a care provider note based upon the at least one medical knowledge base and the care provider diagnosis profile.

4. The system of claim 3, wherein the system generates a plurality of billing information based upon the generated care provider note.

5. The system of claim 2, wherein the system records the selected diagnosis of the care provider and adjusts the care provider diagnosis profile.

6. The system of claim 2, wherein upon receipt of the selected diagnosis, the at least one software application generates a care provider note based upon the care provider diagnosis profile.

7. The system of claim 2, wherein upon receipt of the selected diagnosis, the at least one software application generates a care provider note based upon the at least one medical knowledge base.

8. The system of claim 2, wherein the system generates a treatment plan based upon the selected diagnosis and plurality of patient information.

9. The system of claim 2, wherein the system generates at least one work order based upon the selected diagnosis and plurality of patient information.

10. The system of claim 1, wherein the ranked diagnosis are displayed on the at least one client computer.

11. A method for predicting a diagnosis based on a care provider profile comprising the steps of:
    receiving a plurality of patient information by a computer processor wherein the plurality of patient information includes at least one medical problem;
    analyzing the plurality of patient information and the at least one medical problem by at least one software application on the computer processor against at least one medical related knowledge database in communication with the computer processor;
    the at least one software application identifying at least one diagnosis within the knowledge database based upon the analysis;
    the at least one software application calculating the probability of each of the at least one diagnosis;
    the at least one software application adjusting the calculated probabilities of each diagnosis based on the care provider profile wherein the care provider profile is a learned profile based upon at least one previously selected diagnosis and at least one previously presented diagnosis which was not selected; and
    the at least one software application ranking the at least one diagnosis based upon the adjusted probabilities.

12. The method of claim 11, further comprising the step of the computer processor transmitting the the ranked list of at least one diagnosis to a client computer.

13. The method of claim 12, further comprising the step of receiving a selection of one of the plurality of ranked diagnosis from the client computer.

14. The method of claim 13, further comprising the step of the at least one software application generating a care provider note based upon the selected diagnosis and the care provider profile.

15. The method of claim 14, further comprising the step of the at least one software application generating a plurality of billing information based upon the generated care provider note.

16. The method of claim 13, further comprising the step of the at least one software application adjusting the care provider diagnosis profile based upon the selected diagnosis.

17. The method of claim 13, further comprising the step of the at least one software application generating a care provider note based upon the selected diagnosis and the at least one medical knowledge base.

18. The method of claim 13, further comprising the step of the at least one software application generating a care provider note based upon the selected diagnosis, the at least one medical knowledge base, and the care provider profile.

19. The method of claim 13, further comprising the step of the at least one software application generating a treatment plan based upon the selected diagnosis and plurality of patient information.

20. The method of claim 13, further comprising the step of the at least one software application generating at least one work order based upon the selected diagnosis.

21. An intelligent care provider medical practice system comprising:
    at least one server;
    at least one client computer in communication with the at least one server;
    at least one database in communication with the at least one server, wherein the at least one database has at least one medical knowledge base;
    at least one software application resident on the server which provides:
        a graphical user interface configured to allow entry and receipt of a plurality of patient information and at least one patient health problem from at least one of the at least one a client computer;
        a comparative analysis of the plurality of patient information and at least one patient health problem compared with the at least one medical knowledge base to identify one or more diagnosis;
        a calculation of the probability of each of the identified at least one diagnosis based upon the comparative analysis;
        an adjustment of the calculated probabilities based upon a care provider diagnosis profile wherein the care provider diagnosis profile is a learned diagnosis profile based upon at least one previously selected diagnosis and at least one previously presented diagnosis which was not selected;
        ranking the diagnoses based on the adjusted calculated probability wherein the ranked diagnosis are displayed on the at least one client computer;
    wherein a selection of one of the plurality of ranked diagnosis is received from the at least one client computer and the system adjusts the care provider diagnosis profile based upon the selected diagnosis and the presented diagnosis which were not selected; and
    wherein the at least one software application generates a care provider note based upon the selected diagnosis.

* * * * *